United States Patent
Lavranos

(10) Patent No.: US 11,478,445 B2
(45) Date of Patent: Oct. 25, 2022

(54) METHOD FOR TREATING ACUTE MYELOID LEUKEMIA

(71) Applicant: Bionomics Limited, Eastwood (AU)

(72) Inventor: Tina Lavranos, Thebarton (AU)

(73) Assignee: Bionomics Ltd., Thebarton (AU)

( * ) Notice: Subject to any disclaimer, the term of this patent is extended or adjusted under 35 U.S.C. 154(b) by 69 days.

(21) Appl. No.: 16/758,787

(22) PCT Filed: Oct. 17, 2018

(86) PCT No.: PCT/AU2018/051128
§ 371 (c)(1),
(2) Date: Apr. 23, 2020

(87) PCT Pub. No.: WO2019/079848
PCT Pub. Date: May 2, 2019

(65) Prior Publication Data
US 2021/0177797 A1    Jun. 17, 2021

(30) Foreign Application Priority Data
Oct. 25, 2017    (AU) .................................. 2017904326

(51) Int. Cl.
*A61K 31/343* (2006.01)
*A61P 35/02* (2006.01)
*A61K 31/665* (2006.01)

(52) U.S. Cl.
CPC .......... *A61K 31/343* (2013.01); *A61K 31/665* (2013.01); *A61P 35/02* (2018.01)

(58) Field of Classification Search
None
See application file for complete search history.

(56) References Cited

U.S. PATENT DOCUMENTS

| | | | |
|---|---|---|---|
| 9,006,284 B2 * | 4/2015 | Kremmidiotis | A61P 11/00 514/470 |
| 9,987,293 B2 * | 6/2018 | Eastman | A61K 31/665 |
| 10,137,105 B2 * | 11/2018 | Eastman | A61P 35/02 |

FOREIGN PATENT DOCUMENTS

WO    2015/149105 A1    10/2015

OTHER PUBLICATIONS

Bates et al., "Rapid induction of apoptosis in chronic lymphocytic leukemia cells by the microtubule disrupting agent BNC105", 2016, Cancer Biology & Therapy, 17(3), pp. 291-299. (DOI: 10.1080/15384047.2016.1139245) (Year: 2016).*
Narsimha Reddy Penthala, et al. (2015), "Synthesis, anticancer activity and molecular docking studies on a series of heterocyclic trans-cyanocombretastatin analogues as antitubulin agents" NIH Public Access Manuscript, Eur J. Med. Chem, vol. 92, pp. 212-220.
Danny V. Jeyaraju, et al. (2016), "A novel isoflavone, ME-344, targets the cytoskeleton in acute myeloid leukemia", www.Impactjournals.com/oncotarget, vol. 7 (31), pp. 49777-49785.
Nikhil R. Madadi, et al. (2015) "Synthesis and evaluation of a series of resveratrol analogues as potent anti-cancer agents that target tubulin" Medchemcomm, HHS Public Access, Author Manuscript, vol. 6 (3), pp. 788-794.
Bernard L. Flynn, et al. (2011) "Discovery of 7-Hydroxy-6-methoxy-2-methyl-3-(3,4,5-trimethoxybenzoyl)benzo{b}furan (BNC05), Tubulin Polymerization Inhibitor with Potent Antiproliferative and Tumor Vascular Disrupting Properties", NIH Public Access Author Manuscript, J. Med. Chem, vol. 54(17), pp. 6014-6027.
Gabriel Kremmidiotis, et al. (2010), "BNC105: A novel tubulin polymerization inhibitor that selectively disrupts tumor vasculature and displays single-agent antitumor efficacy", Molecular Cancer Therapeutics, vol. 9(6), pp. 1562-1573.
International Search Report from PCT/AU2018/051128, dated Nov. 15, 2018.

* cited by examiner

*Primary Examiner* — My-Chau T. Tran
(74) *Attorney, Agent, or Firm* — McDonnell Boehnen Hulbert & Berghoff LLP

(57) ABSTRACT

The present invention relates to a method for the treatment of acute myeloid leukemia (AML) with medicaments useful for same. The medicaments can be pharmaceutical compositions or kits comprising compounds of the presently-described formula (I) or a salt, solvate or prodrug thereof. Specific compounds of the invention include 2-methyl-7-hydroxy-3-(3,4,5-trimethoxybenzoyl)-6-methoxybenzofuran which is also known as BNC105 and disodium 6-methoxy-2-methyl-3-(3,4,5-trimethoxybenzoyl)benzofuran-7-yl phosphate which is also known as BNC105P.

8 Claims, 11 Drawing Sheets a)
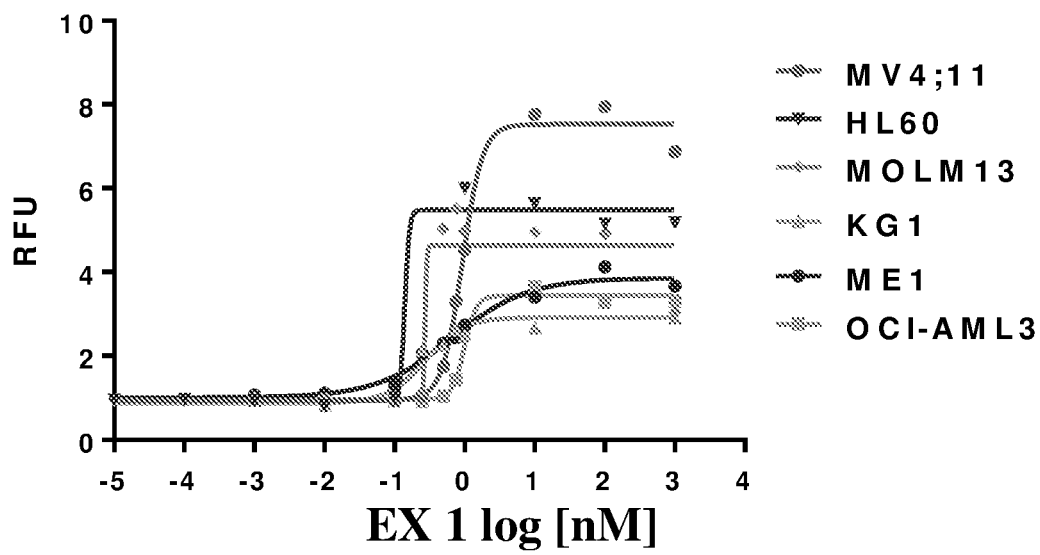
b)
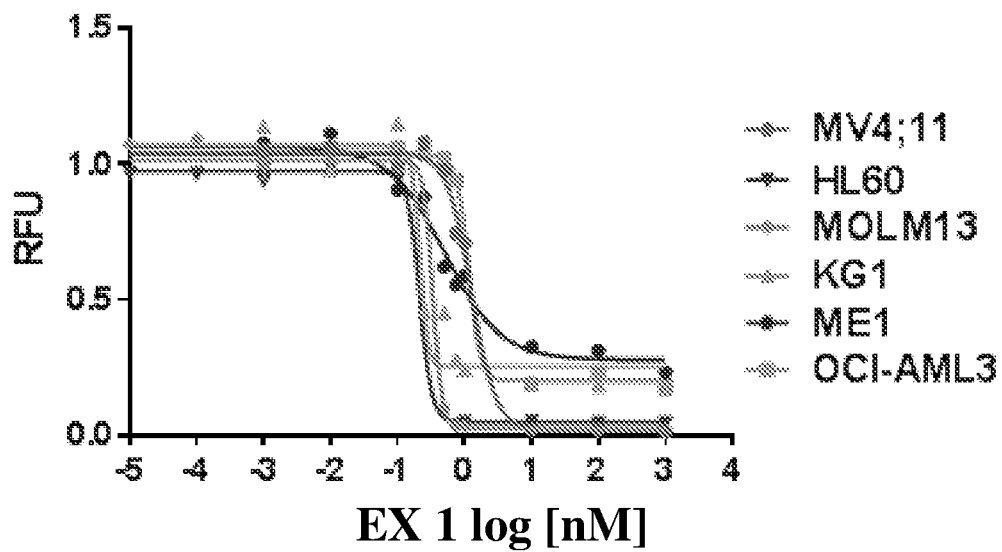
| | HL60 | MOLM13 | MV4;11 | KG1 | ME1 | OCI-AML3 |
|---|---|---|---|---|---|---|
| IC50 | 0.2189 | 0.3397 | 1.286 | 0.2348 | 1.036 | 1.263 |
FIGURE 1

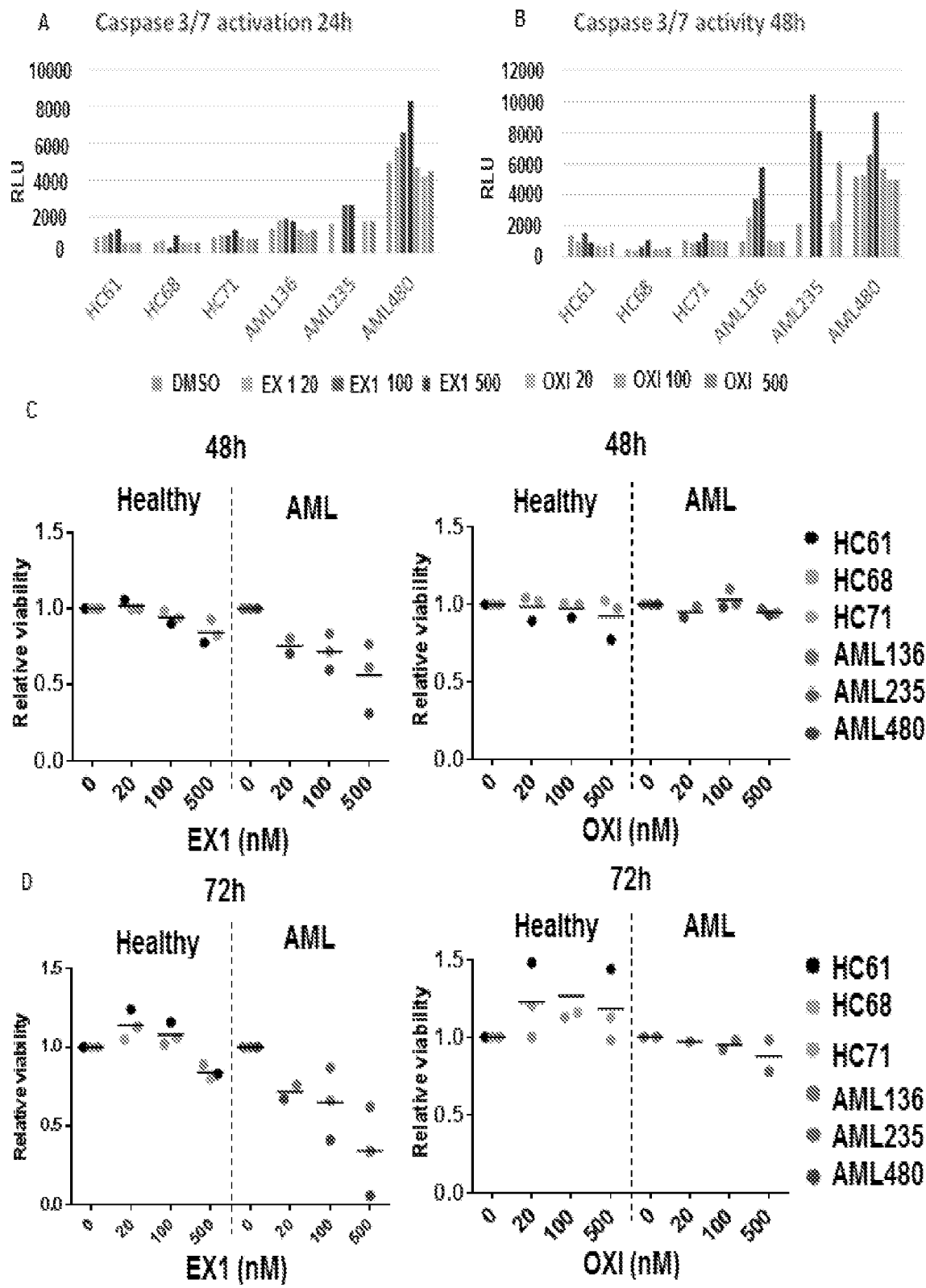
FIGURE 5A-D (continued)

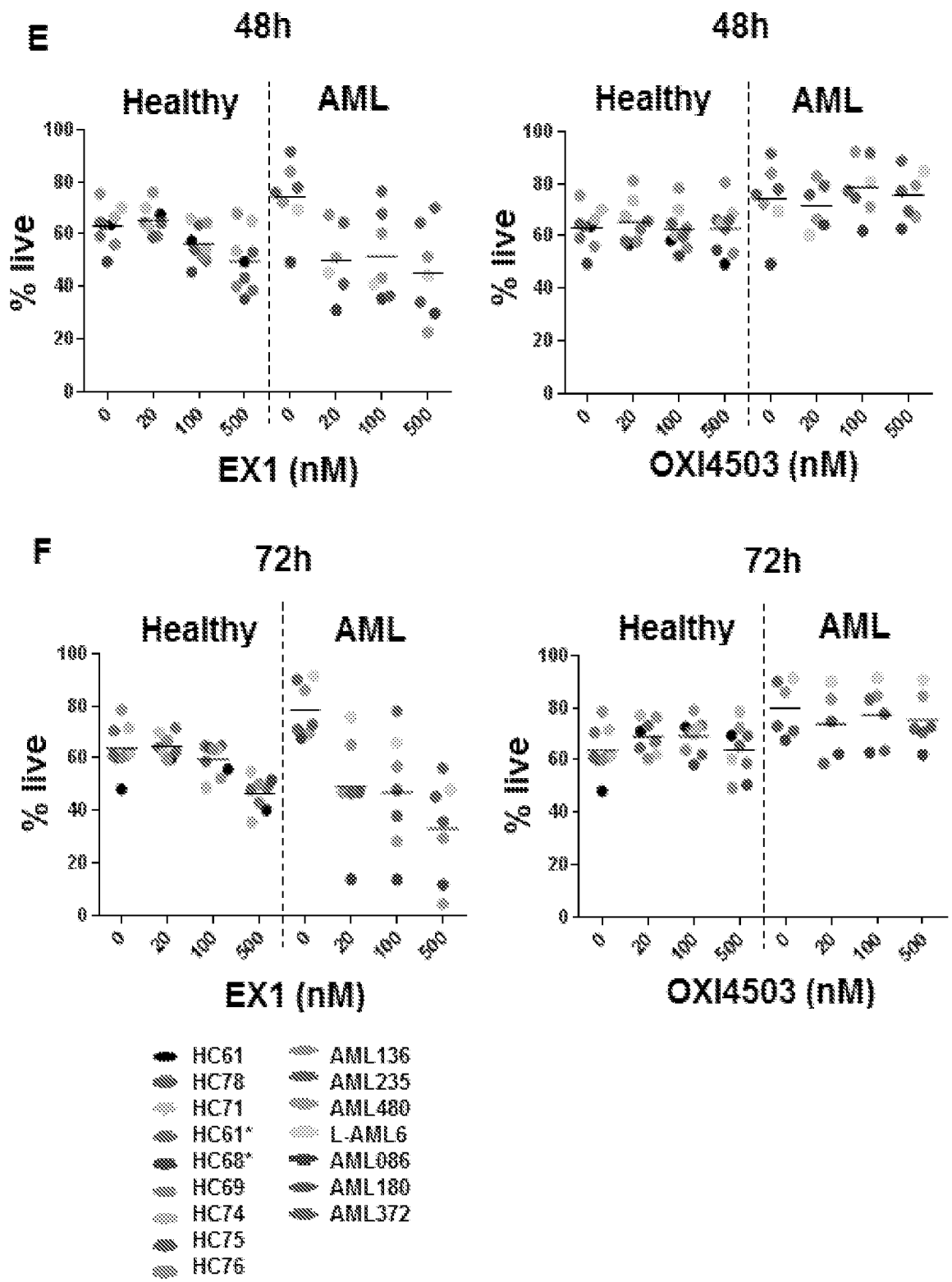
FIGURE 5E-F (end)

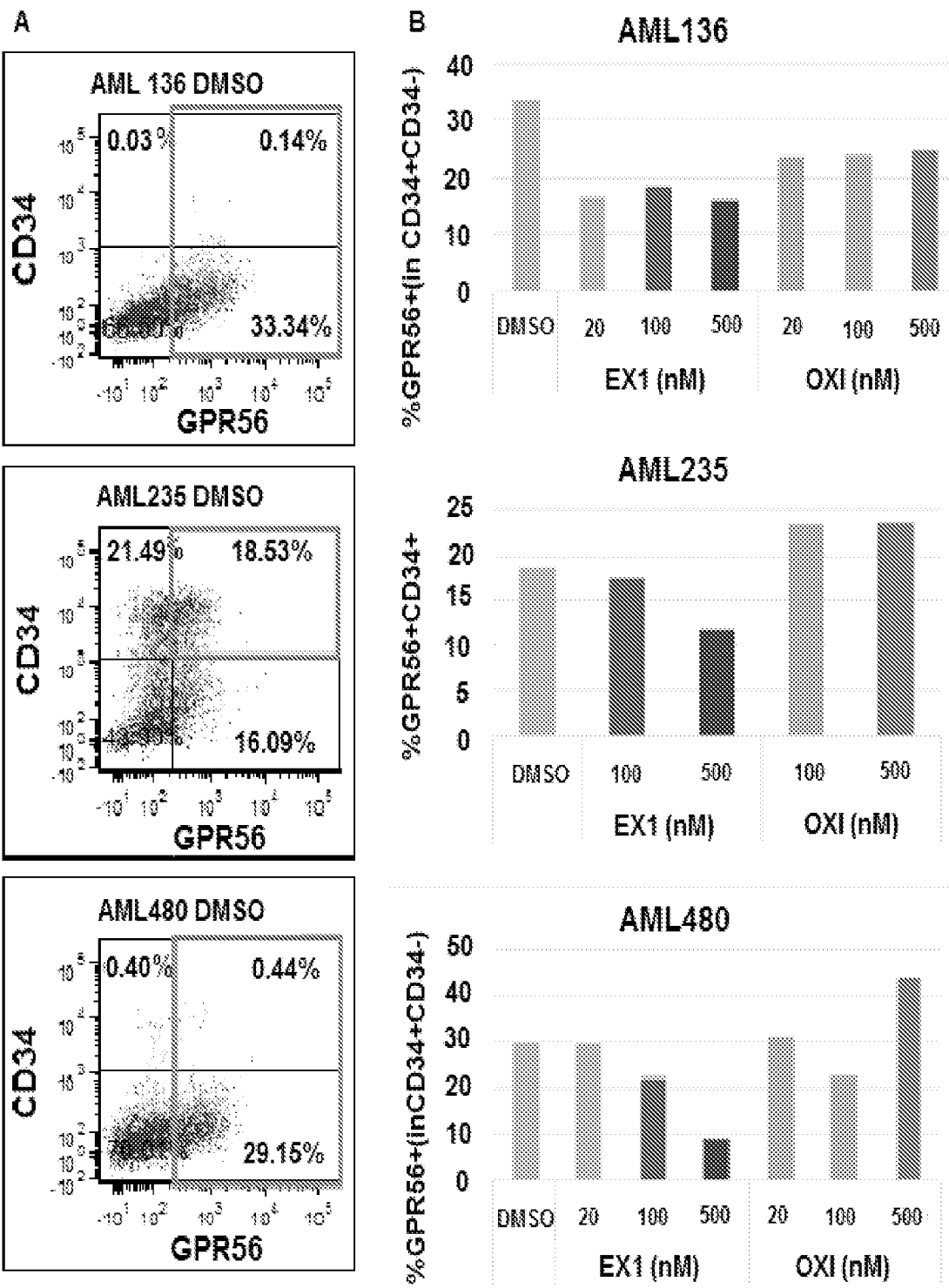
FIGURE 6A-B (continued)

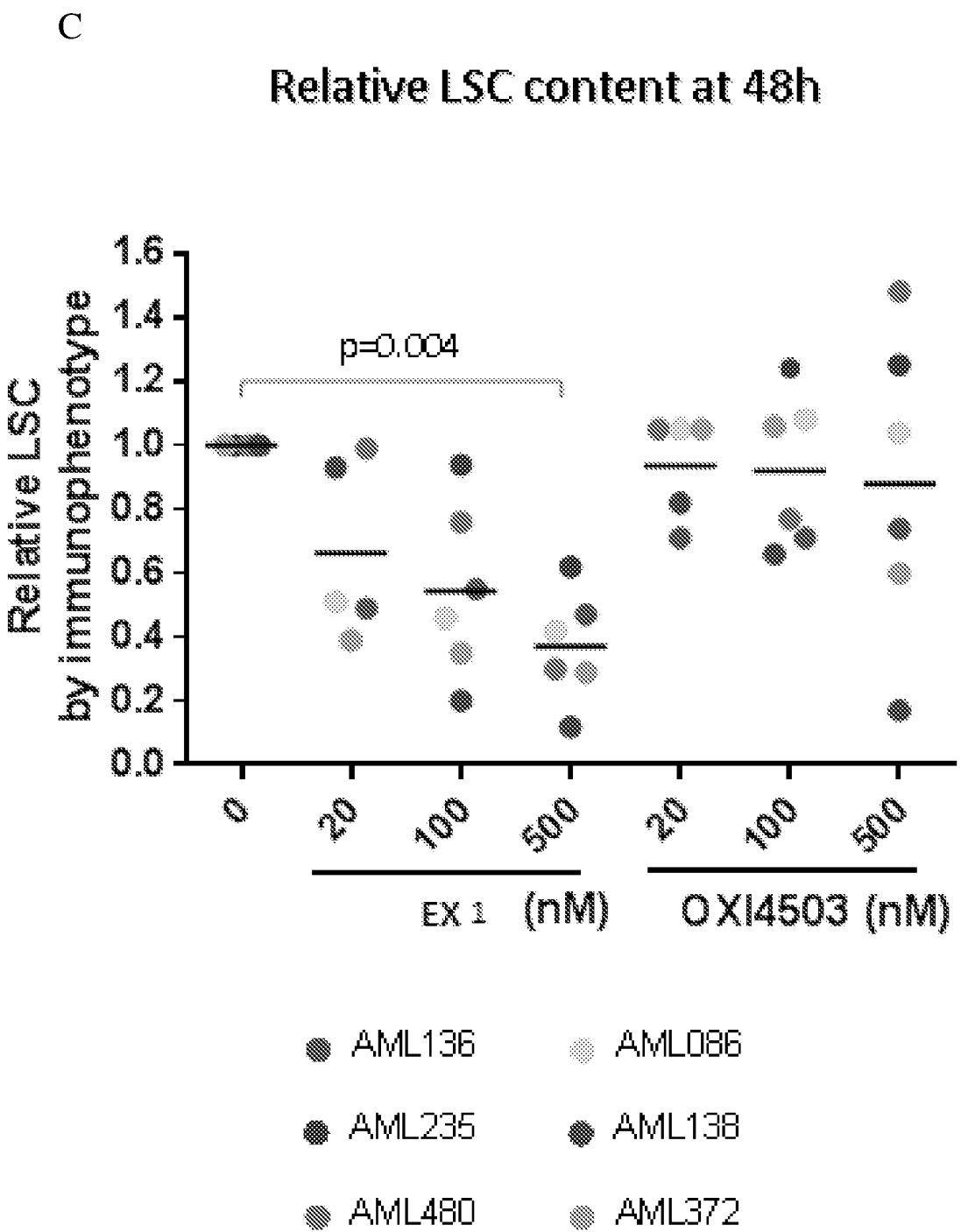
FIGURE 6C (end)

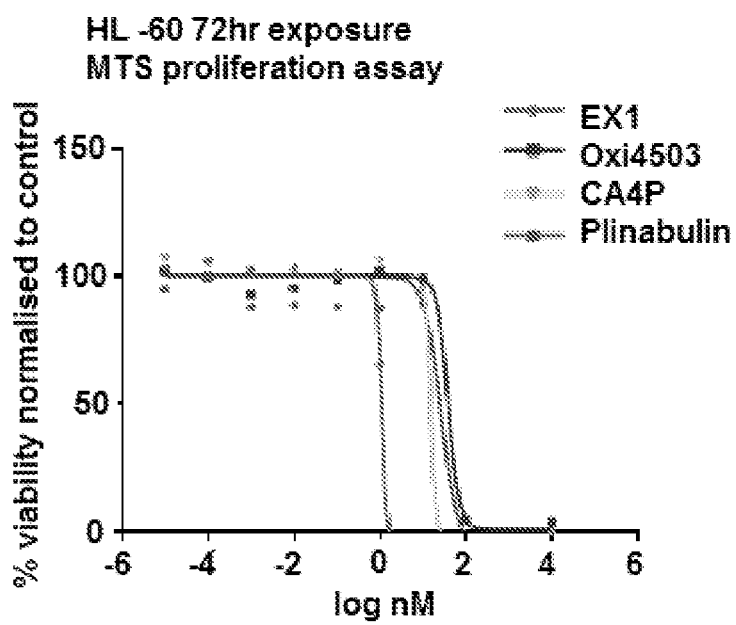
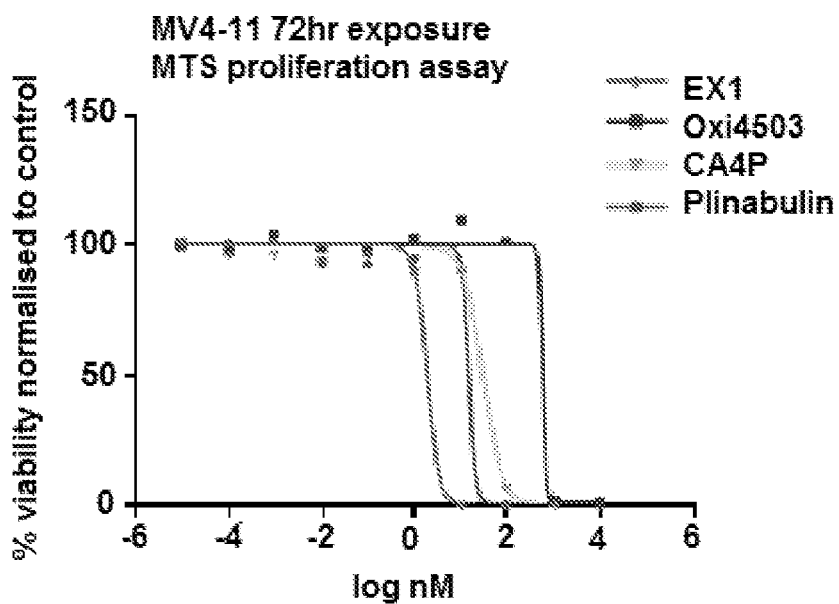
FIGURE 9

METHOD FOR TREATING ACUTE MYELOID LEUKEMIA

CROSS-REFERENCE TO RELATED APPLICATIONS

This application is a U.S. national phase of International Application No. PCT/AU2018/051128, filed Oct. 17, 2018, which claims priority to Australian Patent Application No. 2017904326, filed Oct. 25, 2017, the contents of each of which are incorporated by reference herein in their entirety.

FIELD

The present disclosure teaches methods of specifically treating acute myeloid leukemia (AML) with medicaments useful for same.

BACKGROUND

Cancer is a disorder in which a population of cells has become, in varying degrees, unresponsive to the control mechanisms that normally govern proliferation and differentiation. Leukemia is a cancer of the blood cells, mostly white blood cells. Each year, there are about 60,000 new cases of leukemia in the United States, resulting in about 25,000 deaths. Most patients with leukemia are treated with chemotherapy. Some patients also may have radiation therapy and/or bone marrow transplantation. Leukemia can be either acute or chronic. In acute leukemia, the abnormal blood cells are blasts that remain very immature and cannot carry out their normal functions. The number of blasts increases rapidly, and the disease becomes worse quickly. In chronic leukemia, some blast cells are present, but in general, these cells are more mature and can carry out some of their normal functions. The number of blasts increases less rapidly than in acute leukemia. As a result, chronic leukemia worsens gradually. Leukemia can arise in either of the two main types of white blood cells: lymphoid cells or myeloid cells. When leukemia affects lymphoid cells, it is called lymphocytic leukemia. When myeloid cells are affected, the disease is called myeloid or myelogenous leukemia. The most common types of leukemia include: a) Acute Lymphocytic Leukemia (ALL); b) Acute Myeloid Leukemia (AML); c) Chronic Lymphocytic Leukemia (CLL) and d) Chronic Myeloid Leukemia (CML).

AML accounts for about 30% of all new cases of leukemia (i.e. about 21,000 cases) in the United States resulting in about 10,000 deaths, most of which are in adults. AML generally occurs in older people with the average age of an AML patient being about 67 years. AML is distinguished (such as AML) from other types of leukemia by various techniques such as light microscopy, flow cytometry or fluorescent in situ hybridisation studies. AML may, for example, be diagnosed by establishing a blast percentage of more than 20% leukemic myeloblast in the blood and/or bone marrow under the WHO classification system. It may also be diagnosed by establishing a blast percentage of more than 30% leukemic myeloblast in bone marrow or peripheral blood under the French-American-British (FAB) classification system. Genetic studies may also be performed to look for specific mutations in genes such as FLT3, nucleophosmin, and KIT, which may be present and may affect the outcome of the disease.

Treatment of AML consists primarily of chemotherapy and is made up of two phases: induction therapy and consolidation therapy. The goal of induction therapy is to achieve complete remission by reducing the number of leukemic cells to an undetectable level. The goal of consolidation therapy is to eliminate any residual undetectable disease to achieve a cure. Most induction therapy regimens consist of a combination of daunorubicin and cytarabine. 60%-70% of patients achieve a complete remission with induction chemotherapy, 25-40% requiring more than one course to achieve a complete remission. Optimal treatment for patients who achieve a complete remission is controversial. Chemotherapy is often not curative for patients with AML due to the development of resistance particularly by early leukemia progenitor cells that serve as a reservoir for disease recurrence. In fact, the majority of patients will suffer from relapse within 5 years. The clinical outcome of AML treatment in elderly patients is also poor. An unacceptably high percentage of elderly patients of over 70 years old do not tolerate the current therapy and suffer from treatment-related deaths. Many will also suffer from relapse and die.

There are new targeted therapies that have been developed and approved by FDA to specifically treat AML. For example, the small molecule, enasidenib (Idhifa™) targets isocitrate dehydrogenase 2, which is mutated in about 12% of AML patients. The small molecule Midostaurin (Rydapt™) is able to significantly prolong survival in FLT3-mutated AML patients when combined with conventional induction and consolidation therapies. The anti-CD33 antibody conjugate, Gemtuzumab ozogamicin (Mylotarg™) is also a new therapy that is specifically designed to treat AML patients. A skilled person would understand that the above therapies are designed to specifically treat AML patients. These therapies may or may not work in other leukemia patients (such as in CLL patients). Similar, it is also the case that treatments for CLL may not necessarily be effective for AML or other types of leukemias or indeed other types of myelogenous leukemia.

There is a need for a more efficacious and selective treatments for AML.

SUMMARY

The present disclosure enables an effective treatment for AML predicated in part on the use of a compound of formula (I) or a salt, solvate or prodrug thereof in the selective and preferential induction of apoptosis of AML cells. The compound of formula (I) is represented below:

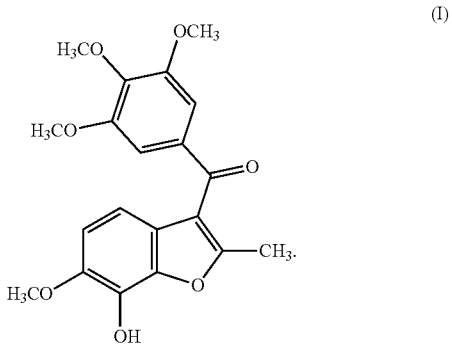 [SMILES: COc1cc(C(=O)c2c(C)oc3c(O)c(OC)ccc23)cc(OC)c1OC]

The compound of formula (I) [2-Methyl-7-hydroxy-3-(3,4,5-trimethoxybenzoyl)-6-methoxybenzofuran] can be prepared by the synthetic methodology described in PCT/

AU2007/000101 (WO 07/087684), the contents of which are incorporated by reference.

Accordingly enabled herein is a method for treating acute myeloid leukemia (AML) in a patient including the step of administering an effective amount of a compound of formula (I) or a salt, solvate or prodrug thereof

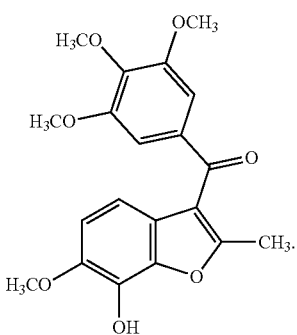

(I)

Further taught herein is the use of a compound of formula (I) or a salt, solvate or prodrug thereof

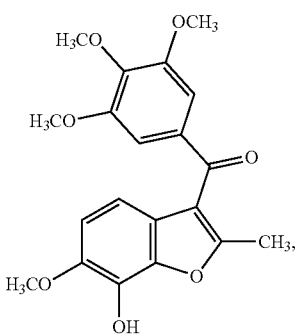

(I)

in the manufacture of a medicament for treating a patient with acute myeloid leukemia (AML).

In a related embodiment, the present specification is instructive on a compound of formula (I) or a salt, solvate or prodrug thereof

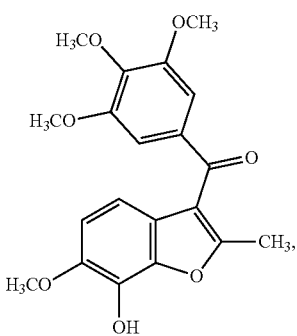

(I)

for use in treating AML in a patient.

In another embodiment the method involves treating a subject in need thereof with an effective amount of the compound of formula (I) in order to induce apoptosis in AML cells.

Reference to "AML" includes its subtypes and its related forms.

BRIEF DESCRIPTION OF THE FIGURES

FIG. 1: Relative fluorescence measured by the CellTox Green assay for cytotoxicity (A) and by CellTiter-Blue assay for viability (B) in AML cell lines treated with indicated doses of EX 1 for 48 h. IC50 doses were determined by the absolute IC50 method in Prism 6. n=2 for MV4; 11 and MOLM13 on both assays, n=1 for remaining cell lines on both assays.

B. Mitochondria O2.-levels, measured by MitoSox fluorescence, after EX 1 treatment of cell lines for 24 h. Values indicate mean fluorescence intensity (MFI) relative to untreated (DMSO) control.

Figure 3:
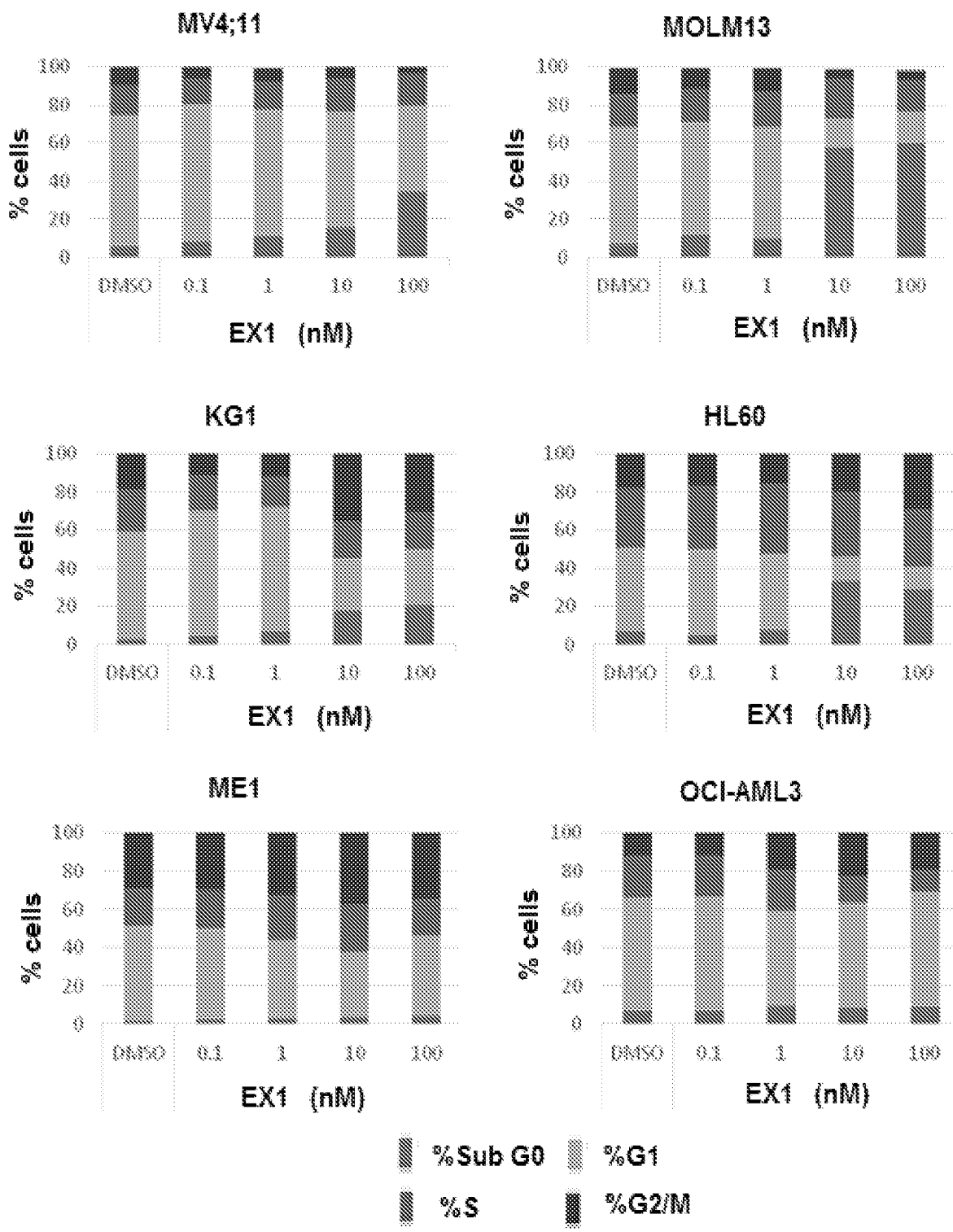

FIG. 3: Cell cycle distribution for the cell lines treated with indicated doses of EX 1 for 24 h. MV4; 11 and MOLM13 show marked apoptosis induction (sub-G0 gate) and G2/M reduction with 10 nM of drug. KG1, HL60, ME1 and OCI-AML3 show G2/M cell cycle arrest. KG1 and HL60 also show increase in sub-G0 population starting at treatment with 10 nM of EX 1.

Figure 4:
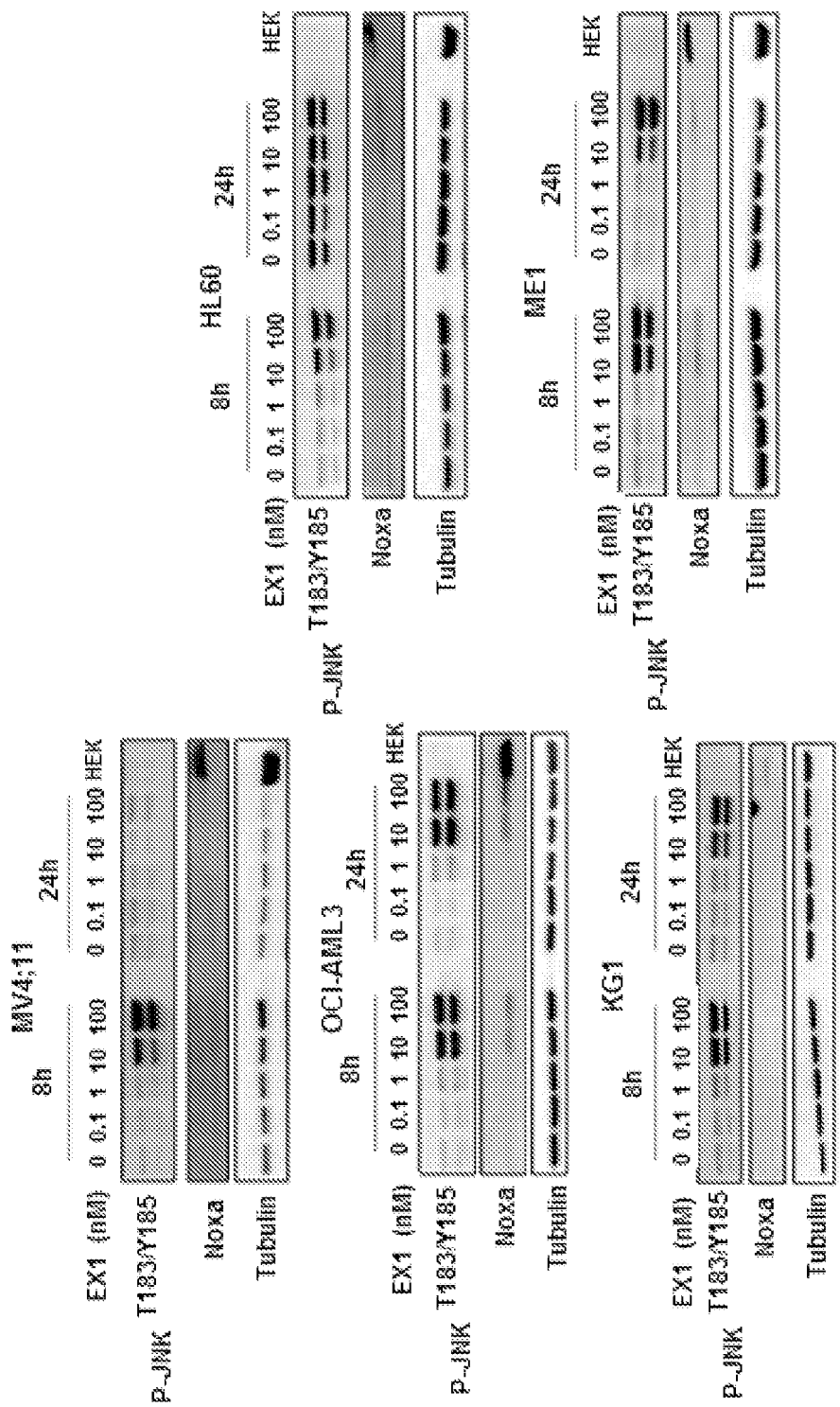

FIG. 4: Western blot was performed with protein lysates from the cell lines treated with EX 1 for 8 h and 24 h at the indicated doses. P-JNK$^{T183/Y185}$ is induced in all cell lines with 10 nM EX 1 at 8 h. Noxa induction is only observed in OCI-AML3 and ME1 lines treated with 10 nM EX 1 at 8 h. HEK293 (HEK) protein lysate was used as positive control for Noxa detection. Tubulin was used as loading control.

FIG. 5: Caspase 3/7 activity was measured in primary MNC samples from healthy controls (HC) and AML samples after 24 h (A) and 48 h (B) of treatment with EX 1 or OXi4503 (doses listed in the legend are in nM). Viability was estimated by flow cytometry after staining with Annexin V/7AAD on the same primary samples after 48 h (C) and 72 h (D) of treatment with either EX 1 or OXi4503. Values plotted are proportion of live cells relative to untreated (DMSO) control. Proportion of live cells corresponds to the double negative cell gate (i.e. negative stain for Annexin V and for 7AAD). Viability as estimated by flow cytometry after staining with Annexin V/7AAD was repeated in additional AML samples (including AML086, AML180, AML372) after 48 h (E) and 72 h (F).

FIG. 6: A. Representative dot plots from flow cytometry analysis to detect the GPR56+ LSC containing population (green gate) in each of the AML samples used (AML136, AML235 and AML480). B. Percentage of GPR56+ cells as determined by the green gates represented on A for the three AML samples after treatment with EX 1 or OXi4503 for 48 h. C Relative amount of LSC as determined by immunophenotype flow cytometry analysis for AML samples after treatment with EX 1 or OXi4503 for 48 h. LSC gating strategy: GPR56+/CD34+ and GPR56+/CD34− for AML136 and AML480, GPR56+/CD34+ for AML235, AML086 and AML138 and CD34+/CD38−/CD93+ for AML372.

Figure 7:
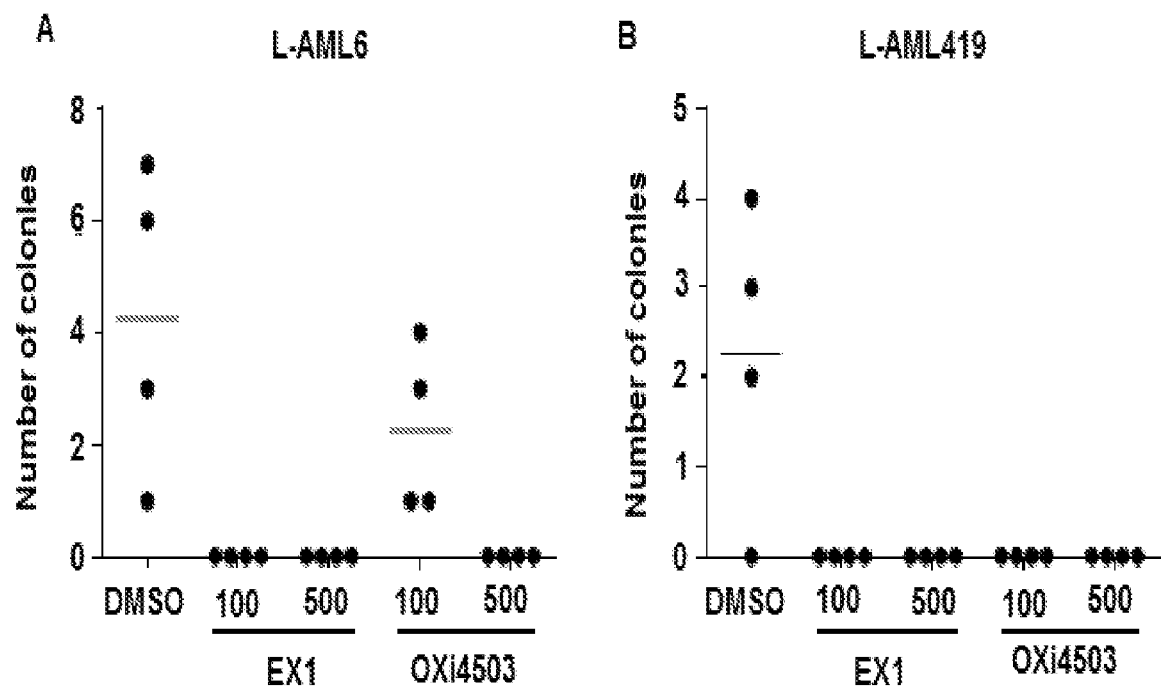

FIG. 7: Colony formation is blocked after treatment of L-AML6 (A) and L-AML419 (B) with EX 1 with the indicated doses. OXi4503 reduces colony formation on L-AML6 at 100 nM but completely inhibits colonies at the highest dose for this sample, and with both doses for L-AML419. Dose indicated are in nM.

Figure 8:
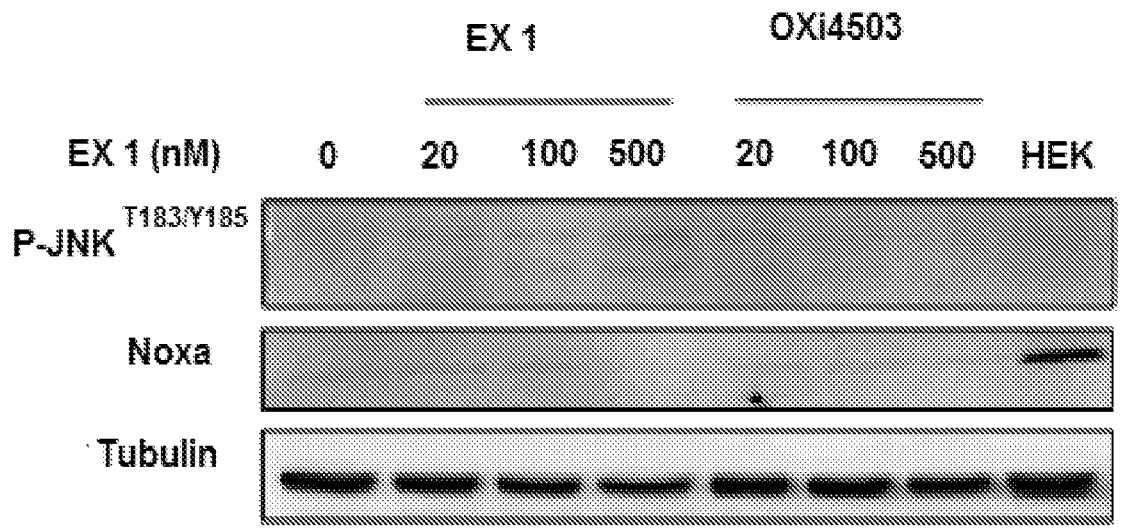

FIG. 8: Western blot was performed with protein lysate from the AML sample L-AML6 treated with EX 1 or OXi4503 48 h at the indicated doses. P-TJNK$^{T183/T185}$ is induced in by 500 nM EX 1 but not by OXi4503. Noxa expression is very low and does not appear to change with any treatment. HEK293 (HEK) protein lysate was used as positive control for Noxa detection. Tubulin as used as loading control.

FIG. 9: MTS proliferation assays were performed showing that EX 1 is at least 10 times more potent than any other VDAs in HL-60 and MV4-11 cell lines after 72 h exposure to the drugs.

DETAILED DESCRIPTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

As used in the subject specification, the singular forms "a", "an" and "the" include the plural aspects unless the context clearly dictates otherwise. Thus, for example, reference to "a AML cell" includes a single cell, as well as two or more cells; reference to "an agent" includes a single agent, as well as two or more agents; reference to "the disclosure" includes a single and multiple aspects taught by the disclosure; and so forth. Aspects taught and enabled herein are encompassed by the term "invention". All such aspects are enabled within the width of the present invention.

The present disclosure teaches that the compounds of formula (I) are potent tubulin polymerisation inhibitors (TPIs), which induces cancer cell death via upregulation of pro-apoptotic proteins. An important aspect of the compounds of formula (I) is the combination of the specific C-6 and C-7 substituents together with the C-2 Q-group (especially C-2 methyl) which appears to confer greater potency and selectivity when compared to other structurally related TPI compounds.

It will be appreciated that the compound of formula (I) can be administered to a subject as a pharmaceutically acceptable salt thereof. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. In an embodiment, the method described herein includes within its scope cationic salts e.g. sodium or potassium salts, or alkyl esters (e.g. methyl, ethyl) of the phosphate group.

It will also be appreciated that any compound that is a prodrug of a compound of formula (I) is also within the scope and spirit of the therapeutic protocol herein described. The term "pro-drug" is used in its broadest sense and encompasses those derivatives that are converted in vivo to a compound of the invention (for instance, a compound of formula (I). Such derivatives would readily occur to those skilled in the art, and include, for example, compounds where the free hydroxy group (for instance at C-7 position or $R^{1D}$) is converted into an ester, such as an acetate or phosphate ester, or where a free amino group (for instance at C-7 position or $R^{1D}$) is converted into an amide (e.g., α-aminoacid amide). Procedures for esterifying, e.g. acylating, the compounds are well known in the art and may include treatment of the compound with an appropriate carboxylic acid, anhydride or chloride in the presence of a suitable catalyst or base. One prodrug is a disodium phosphate ester. The disodium phosphate ester (e.g., a C-7 disodium phosphate ester of a compound of formula I) of the compound of the present invention may be useful in increasing the solubility of the compounds. This would, for instance, may allow for delivery of the compound in a benign vehicle like saline. The disodium phosphate ester may be prepared in accordance with the methodology described in Pettit, G. R., et al, *Anticancer Drug Des.*, 1995, 10, 299. Other texts which generally describe prodrugs (and the preparation thereof) include: *Design of Prodrugs*, 1985, H. Bundgaard (Elsevier); *The Practice of Medicinal Chemistry*, 1996, Camille G. Wermuth et al., Chapter 31 (Academic Press); and *A Textbook of Drug Design and Development*, 1991, Bundgaard et al., Chapter 5, (Harwood Academic Publishers).

Accordingly in an embodiment the compound of formula (I) is a compound represented as:

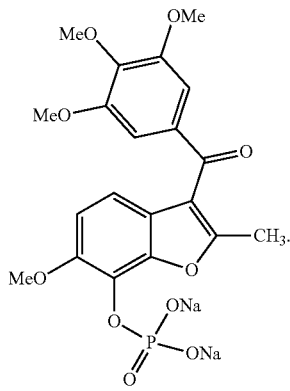

The compounds of formula (I) (or a salt or prodrug thereof) may be in crystalline form either as the free compound or as a solvate (e.g. hydrate) and it is intended that both forms are within the scope of the present invention. Methods of solvation are generally known within the art.

An "effective amount" is intended to mean that the amount of formula (I), or a salt or prodrug thereof when administered to a subject in need of such treatment, is sufficient to effect treatment for AML. Thus, for example, a therapeutically effective amount is a quantity sufficient to reduce or alleviate AML. Reference to a subject includes a human of any age.

Treatment includes at least partially attaining the desired effect, or delaying the onset of, or inhibiting the progression of, or halting or reversing altogether the onset or progression of AML.

In an embodiment, treatment is assessed by reduction of blast counts (<5%) and restoration of normal blood counts.

Reference to "AML" includes its subtypes and its related forms. The AML subtype may be an M0, M1, M2, M3, M4, M4eo, M5, M6 or M7 subtype under the FAB classification system. AML may also refer to AML progenitor cells. The compounds of formula (I) (or a salt or prodrug thereof) may specifically target or eliminate AML cells of any one of the above AML subtypes. The compounds of formula (I) (or a salt or prodrug thereof) may also specifically target or eliminate AML progenitor cells.

The compounds of formula (I) (or a salt or prodrug thereof) may be administered at any stage of treatment of the patient, including the induction, post-induction (or consolidation) and maintenance stages of treatment, either as a monotherapy, or more preferably, in combination with other induction, consolidation and/or maintenance therapies, including surgery, radiation or chemotherapies (e.g., antimetabolites like cytarabine (ara-C); anthracyclines such as daunorubicin, doxorubicin or idarubicin; and other drugs such as 6-thioguanine, gentuzumab ozogamicin (Mylotarg), midostaurin (Rydapt), enasidenib (Idhifa), SCH-727965 (Dinaciclib), and/or a colony stimulating factors such as G-CSF or GM-CSF. As such, the present invention contemplates combination treatments with the above known drugs (anti-cancer agents) in order to achieve a better patient outcome.

In one embodiment, the compounds of formula (I) (or a salt or prodrug thereof) are able to specifically target or eliminate AML cells (including AML progenitor cells) during the induction and/or consolidation phases, leading to a complete remission and elimination of any residual undetectable disease to achieve a cure.

The administration of the pharmaceutical combination of the present invention may result not only in a beneficial effect, e.g., an additive or synergistic therapeutic effect, for instance, with regard to alleviating, delaying progression of or inhibiting or ameliorating the symptoms of AML, but also in further surprising beneficial effects. Such other effects may include fewer adverse side effects, an improved quality of life or a decreased morbidity, compared with a monotherapy applying only one of the pharmaceutically active ingredients used in the combination of the present invention.

A further benefit of the instant therapeutic protocol is that lower doses of the active ingredients of the compound of formula (I) may be used. The dosages need not only be smaller but may also be applied less frequently, which may diminish the incidence or severity of side effects.

In addition, the compounds of formula (I) may be used in combination with the Standard of Care treatment. This allows the Standard of Care treatment to be administered at a lower dose, thus reducing the incidence or severity of side effects.

The treatment protocol herein described may further involve selecting a patient for treatment based on certain clinical parameters such as age, level of progression of the disease and/or other factors. In addition, patients are generally monitored for progression of AML after initiation of treatment. Hence, after cessation of treatment, additional treatment may be required subsequently dependent on state or level of remission.

The term "administration" relates to the administration of a compound of formula (I), or salt or prodrug thereof, to a single patient. In a combination therapy if its intended to include treatment regimens in which the agents are not necessarily administered by the same route of administration or at the same time. Accordingly, combination partners may be administered together, one after the other or separately in one combined unit dosage form or in two separate unit dosage forms. The unit dosage form may also be a fixed combination such as a pharmaceutical composition which comprises both partners.

In an embodiment, a therapeutically effective amount of a compound of formula (I) may be administered alone or simultaneously or sequentially with another agent and in any order, and the components may be administered separately or as a fixed combination. For example, the method of treating AML according to the invention may comprise: (i) administration of a first combination partner in free or pharmaceutically acceptable salt form or prodrug form; and (ii) administration of a second combination partner in free or pharmaceutically acceptable salt form or prodrug form, simultaneously or sequentially in any order, in jointly therapeutically effective amounts, preferably in synergistically effective amounts, e.g., in daily or intermittent dosages corresponding to the amounts described herein. The individual combination partners of the combination of the invention may be administered separately at different times during the course of therapy or concurrently in divided or single combination forms. The term administering also encompasses the use of a pro-drug of a combination partner that converts in vivo to the combination partner as such. The present invention is therefore to be understood as embracing all such regimens of simultaneous or alternating treatment and the term "administering" is to be interpreted accordingly.

As such it will be appreciated that a combination of partners may be presented as a "kit of parts" for use in the treatment of AML. The kit may comprise a package where the combination partners are supplied separately for co-administration with instructions for use in the particular therapy.

The effective dosage may vary depending on the particular compound or pharmaceutical composition employed, the mode of administration, the condition being treated, the severity of the condition being treated. Thus, the dosage regimen is selected in accordance with a variety of factors including the route of administration and the renal and hepatic function of the patient. A physician of ordinary skill can readily determine and prescribe the effective amount of the single active required to alleviate, counter or arrest the progress of the condition.

Daily dosages will, of course, vary depending on a variety of factors, e.g., the compound chosen, the particular condition to be treated and the desired effect. In general, however, satisfactory results are achieved on administration of a compound of formula (I) at daily dosage rates of about 0.05 to 18 mg/kg per day, e.g. 0.4 to 16 mg/kg per day, as a single dose or in divided doses. The compound may be administered by any conventional route, in particular enterally or parenterally, e.g., in the form of injectable solutions or suspensions.

The compound of formula (I) may be administered to a human in a daily dosage range of 0.5 to 1000 mg. Suitable unit dosage forms for parental administration comprise from about 0.1 to 500 mg active ingredient, preferably 5-50 mg/day, more preferably 5-20 mg/day, and most preferably about 7-12 mg/day, together with one or more pharmaceutically acceptable diluents or carriers therefore.

A further benefit is that lower doses of the active ingredient can be used, e.g., that the dosages need not only often be smaller but are also applied less frequently, or can be used in order to diminish the incidence of side effects. This is in accordance with the desires and requirements of the patients to be treated.

The invention also relates to pharmaceutical compositions which comprise compositions of formula (I) or salts or prodrugs thereof, which for instance, contain, e.g., from about 0.1% to about 99.9%, including from about 1% to about 60%, of the active ingredient(s).

The composition, for instance, an IV solution, may contain any diluents or excipients. These include all conventional solvents, dispersion media, antibacterial agents, surfactants and isotonic agents and the like. It will be understood that the compositions of the invention may also include other supplementary physiologically active agents.

The carrier must be pharmaceutically "acceptable" in the sense of being compatible with the other ingredients of the composition and not injurious to the subject. Compositions include those suitable for parental (i.e. intravenous) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

In an embodiment unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Synthetic Protocols

Preparation of 2-Bromo-7-acetoxy-3-(3,4,5-trimethoxybenzoyl)-6-methoxybenzofuran

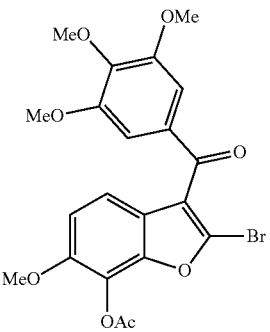 [SMILES: COc1cc(C(=O)c2c(Br)oc3c(OC(C)=O)c(OC)ccc23)cc(OC)c1OC]

Step 1: 2-t-Butyldimethylsilyl-3-(t-butyldimethylsilyloxymethylene)-6-methoxy-7-isopropoxybenzofuran (Larock Coupling)

A suspension of 2-isopropoxy-3-methoxy-5-iodophenol (4.41 mmol), 1-(tert-butyldimethylsilyl)-3-(tert-butyldimethylsilyloxy)propyne (1.5 g, 5.28 mmol), lithium chloride (189 mg, 4.45 mmol) and sodium carbonate (2.34 g, 22.08 mmol) in dry dimethylformamide (5 mL) at 100° C. was deoxygenated 4 times by evacuation and backfilling with nitrogen. Palladium acetate (135 mg, 0.60 mmol) was added and the reaction vessel was degassed twice with nitrogen. The reaction mixture was then stirred at this temperature for 4 hours (tlc) and the solvent was removed by distillation under vacuum. The residue was dissolved in ethyl acetate (75 mL), stirred well, filtered and treated with triethylamine (5 mL). The solution was concentrated onto silica gel (10 g) and purified by flash chromatography (silica gel, eluent=hexane/diethyl ether/triethylamine; 95:5:1%) to afforded the title compound as a yellow oil (1.45 g, 96%); $^1$H NMR (300 MHz, CDCl$_3$) δ 7.24 (d, 1H, J=8.45 Hz), 6.88 (d, 1H, J=8.47 Hz), 4.80 (s, 2H, CH$_2$), 4.73 (m, 1H), 3.88 (s, 3H, OMe), 1.36 (d, 6H, J=6.17 Hz), 0.94 (s, 9H), 0.92 (s, 9H), 0.35 (s, 6H), 0.12 (s, 6H).

Step 2: 2-t-Butyldimethylsilyl-3-formyl-6-methoxy-7-isopropoxybenzofuran

To a solution of 2-t-butyldimethylsilyl-3-(t-butyldimethylsilyloxymethylene)-6-methoxy-7-isopropoxybenzofuran (2.69 mmol) in methanol (100 mL) was added concentrated hydrochloric acid (200 µL) and the reaction was stirred for 30 minutes (monitored by tlc), quenched with triethylamine (2 mL) and the solvent removed by distillation under vacuum. The residue was dissolved in dichloromethane (20 mL), washed with water (10 mL), dried over magnesium sulfate, concentrated under vacuum and co-distilled with toluene (20 mL). The crude product was dissolved in dry dichloromethane (4 mL) and added to a stirred solution of Collin's reagent (chromium trioxide (1.01 g), pyridine (1.65 mL) in dry dichloromethane (30 mL)). The suspension was stirred for 10 minutes, filtered and the residue washed with diethyl ether (20 mL). The filtrate was concentrated onto silica (10 g) and purified by flash chromatography (silica gel, eluent=hexane/diethyl-ether/triethylamine (90:9:1) to afford the title compound as a light yellow oil (503 mg, 48%); $^1$H NMR (300 MHz, CDCl$_3$) δ 10.25 (s, 1H, CHO), 7.79 (d, 1H, J=8.45 Hz), 6.98 (d, 1H, J=8.46 Hz), 4.65 (m, 1H), 3.89 (s, 3H, OMe), 1.35 (d, 6H, J=6.17 Hz), 0.97 (s, 9H), 0.45 (s, 6H).

Step 3: 2-t-Butyldimethylsilyl-3-(3,4,5-trimethoxybenzoyl)-6-methoxy-7-isopropoxybenzofuran To a stirred solution of 3,4,5-trimethoxyiodobenzene (377 mg, 1.27 mmol) in dry tetrahydrofuran (1 mL) at −78° C. under nitrogen was added n-butyllithium (795 µL, 1.59 mmol, 2M solution in cyclohexane) and the reaction mixture was stirred at this temperature for 40 minutes. After this time a solution of 2-t-butyldimethylsilyl-3-formyl-6-methoxy-7-isoproxybenzofuran (1.07 mmol) in dry tetrahydrofuran (1 mL) was added to the reaction dropwise via syringe pipette. The reaction mixture was stirred at −60° C. for 20 minutes and then allowed to warm to 0° C., stirred for 10 minutes, quenched with saturated ammonium chloride solution (2 mL) and diluted with ethyl acetate (20 mL). The organic layer was washed with water (10 mL), dried over magnesium sulfate and the solvent was removed under vacuum to give a residue that was co-distilled with toluene. The crude product (908 mg) was dissolved in dry tetrahydrofuran (10 mL) and treated with 2,3-dichloro-5,6-dicyano-1,4-benzoquinone (900 mg, 1.59 mmol) was added. The reaction mixture was stirred at room temperature for 16 hours (monitored by tlc) and then loaded onto silica (10 g) and purified by flash chromatography (silica gel, eluent=hexane/diethyl ether/triethylamine, 90:9:1) to afford the title compound as a light yellow oil (498 mg, 69%); $^1$H NMR (300 MHz, CDCl$_3$) δ 7.14 (s, 2H, benzoyl Hs), 6.81 (d, 1H, J=8.64 Hz), 6.77 (d, 1H, J=8.64 Hz) 4.74 (m, 1H), 3.93 (s, 3H, OMe), 3.86 (s, 3H, OMe), 3.78 (s, 6H, 2× OMe), 1.39 (d, 6H, J=6.14 Hz), 1.01 (s, 9H), 0.26 (s, 6H).

Step 4: 2-(tert-butyldimethylsilyloxy)-7-acetoxy-3-(3,4,5-trimethoxybenzoyl)-6-methoxybenzofuran To a stirred solution of 2-(t-butyldimethylsilyloxy)-7-isopropoxy-3-(3,4,5-trimethoxybenzoyl)-6-methoxy-benzofuran (160 mg, 0.31 mmol) in dry DCM (2 mL) at room temperature under nitrogen was added solid aluminium trichloride (83 mg, 0.62 mmol) and the reaction mixture was stirred for 15 minutes (monitored by tlc). The reaction was quenched with a saturated solution of ammonium chloride, extracted with dichloromethane and dried over magnesium sulfate. The solvent was removed by distillation and residue was dried by azeotropic removal of water with toluene. The crude product was dissolved in pyridine (2 mL), acetic anhydride (1 mL) was added and reaction mixture was stirred for 2 hours at room temperature. The solvent was distilled under vacuum and the residue was loaded onto silica gel (1 g) and purified by column chromatography (silica gel, eluent, hexane:diethyl-ether; 80:20) (134 mg, 84%); $^1$H NMR (300 MHz, CDCl$_3$) δ 7.14 (s, 2H, benzoyl Hs), 6.98 (d, 1H, J=8.72 Hz), 6.85 (d, 1H, J=8.72 Hz), 3.93 (s, 3H, OMe), 3.86 (s, 3H, OMe), 3.80 (s, 6H, 2×OMe), 2.41 (s, 3H), 0.99 (s, 9H), 0.25 (s, 6H).

Step 5: 2-Bromo-7-acetoxy-3-(3,4,5-trimethoxybenzoyl)-6-methoxybenzofuran

To a stirred solution of 2-t-butyldimethylsilyl-7-acetoxy-3-(3,4,5-trimethoxybenzoyl)-6-methoxybenzofuran (120 mg, 0.44 mmol) in 1,2-dichloroethane (1 mL) at room temperature under nitrogen was added bromine (12 µl, 0.44 mmol) dropwise and the reaction mixture was stirred at this temperature for 10 minutes. After this time the reaction was quenched with saturated sodium thiosulfate solution, extracted with ethyl acetate (20 mL), dried over magnesium sulfate and the solvent removed by distillation under vacuum. The crude product was purified by silica gel column chromatography (eluent=Hexane:diethyl ether; 8:2-7:3) to afford the title compound as a colourless crystalline solid (91 mg, 81%); $^1$H NMR (300 MHz, CDCl$_3$) δ 7.40 (d, 1H, J=8.70 Hz), 7.14 (s, 2H, benzoyl-Hs), 6.98 (d, 1H, J=8.75 Hz), 3.94 (s, 3H, OMe), 3.89 (s, 3H, OMe), 3.86 (s, 6H, 2×OMe), 2.43 (s, 3H); $^{13}$C NMR (75 MHz, CDCl$_3$) δ 187.95 (CO), 167.71, 152.75, 149.54, 147.49, 142.59, 131.92, 131.80, 123.91, 121.84, 119.89, 117.72, 109.89, 106.92, 60.69, 56.61, 56.00, 20.09.

Example 1

Preparation of 2-Methyl-7-hydroxy-3-(3,4,5-trimethoxybenzoyl)-6-methoxybenzofuran

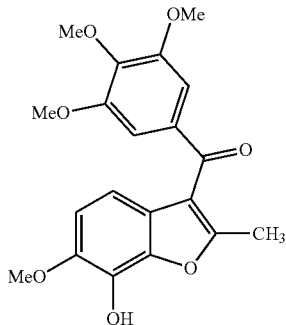 [SMILES: COc1cc(C(=O)c2c(C)oc3c(O)c(OC)ccc23)cc(OC)c1OC]

Preparation A

To a stirred solution of 2-Bromo-7-acetoxy-3-(3,4,5-trimethoxybenzoyl)-6-methoxybenzofuran (20 mg, 0.042 mmol), methyl-boronic acid (40 mg, 0.67 mmol), in 1,4-dioxane (2 mL) at 90° C. was added tetrakis-triphenylphosphine palladium (11 mg, 0.01 mmol) followed by the addition of a solution of sodium bicarbonate (40 mg, 0.48 mmol) in distilled water (0.5 mL). The reaction mixture turned red after 5 minutes. After 2 hours (tlc) the reaction mixture was brought to room temperature and was added saturated ammonium chloride (2 mL) and diluted with dichloromethane (20 mL). The organic layer was separated and washed with water, dried over magnesium sulfate and the solvent was removed by distillation under vacuum. The residue was purified by PTLC (eluent=Dichloromethane/Methanol, 1:1) to give the title compound (acetate cleaved during reaction) as a fluffy white solid; (3 mg, 19%).

Preparation B (Negishi Coupling)

To a stirred solution of zinc-bromide (592 mg, 2.63 mmol) in dry THF (1.5 mL) at 0° C. was added the solution of methyl lithium (1.6 M solution in diethyl-ether, 2.6 mL, 4.15 mmol) and the reaction mixture was stirred for 2 hours. Solid 2-bromo-7-acetoxy-3-(3,4,5-trimethoxybenzoyl)-6-methoxy-benzofuran (300 mg, 0.63 mmol) was added and the ether was removed under vacuum and to the rest suspension was added dichlorobis(triphenylphosphine)palladium catalyst (21 mg) and catalytic amount of copper (I) iodide. The reaction mixture was stirred at room temperature for 36 hours (monitored by tlc), quenched with saturated ammonium chloride solution and extracted with dichloromethane (10 mL), dried over magnesium sulfate and solvent distilled under vacuum and the product was purified by silica gel column (eluent=hexane/ethyl acetate; 8:2). The product was crystallized in methanol (106 mg, 46%); $^1$H NMR (300 MHz, CDCl$_3$) δ 7.09 (s, 2H, benzoyl Hs), 6.93 (d, 1H, J=8.54 Hz), 6.83 (d, 1H, J=8.56 Hz), 5.70 (bs, 1H, OH), 3.93 (s, 3H, OMe), 3.92 (s, 3H, OMe), 3.83 (s, 6H, 2×OMe), 2.54 (s, 3H, 2-Me)

Example 2

Preparation of Disodium 6-methoxy-2-methyl-3-(3,4,5-trimethoxybenzoyl)benzofuran-7-yl phosphate

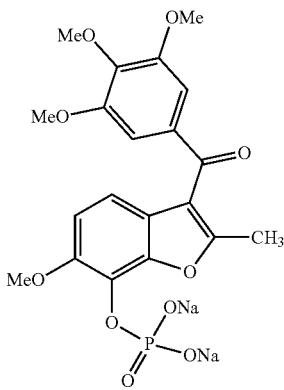

Step 1: Dibenzyl 6-methoxy-2-methyl-3-(3,4,5-trimethoxybenzoyl)benzofuran-7-yl phosphate To a mixture of 0.081 g (0.22 mmol) of (7-hydroxy-6-methoxy-2-methylbenzofuran-3-yl)(3,4,5-trimethoxyphenyl)methanone, 0.086 g (0.261 mmol) of carbon tetrabromide and 0.063 ml (0.283 mmol) of dibenzylphosphite in 2.5 ml of anhydrous acetonitrile 0.046 ml of anhydrous triethylamine was added dropwise at 0° C. under nitrogen atmosphere. The resulting mixture was stirred for 2 h at room temperature, then diluted to 20 ml with ethyl acetate, washed with water brine, dried over anhydrous magnesium sulfate, filtered off and evaporated to dryness under reduced pressure. The residue was purified by flash column chromatography (dichloromethane/ethyl acetate, 9:1) to give the title compound as a colorless foam (0.13 g, 94%); $^1$H NMR (CDCl$_3$) δ 2.42 (s, 3H, Me-2); 3.83 (s, 1H, OMe); 3.93 (s, 3H, OMe); 5.33 (m, 4H, CH$_2$Ph); 6.89 (d, CH aromatic, J=8.7 Hz); 7.21 (dd, 1H, CH aromatic, J=8.72 Hz; J=1.2 Hz); 7.08 (s, 2H, CH aromatic); 7.29-7.43 (m, 10H, CH aromatic).

Step 2: Disodium 6-methoxy-2-methyl-3-(3,4,5-trimethoxybenzoyl)benzofuran-7-yl phosphate To a stirred solution of 0.122 g (0.193 mmol) of the product from Step 1 in 1 ml of anhydrous acetonitrile 0.075 ml (0.58 mmol) of bromotrimethylsilane was added at −5° C. under nitrogen atmosphere. The resulting mixture was stirred for 1 h at 0° C., then evaporated to dryness in vacuo. The residue was diluted to 5 ml with anhydrous methanol and pH of the solution was brought up about 10 by the addition of sodium methoxide. After evaporation of the resulting mixture under reduced pressure the solid residue was washed with anhydrous isopropanol (4×1.5 ml) and anhydrous ethanol (3×1.5 ml) and dried under vacuum to give 0.062 g (65% yield) of title compound as an colorless solid; $^1$H NMR (D$_2$O) δ 2.37 (s, 3H, Me-2); 3.76 (s, 6H, OMe); 3.79 (s, 3H, OMe); 3.82 (s, 3H, OMe); 4.66 (s, H$_2$O); 6.93 (d, 1H, CH aromatic, J=8.6 Hz); 7.04 (d, 1H, CH aromatic, J=8.6 Hz); 7.10 (s, 2H, CH aromatic).

Biological Data

Materials and Methods

Tissue Culture—Cell Lines

Cryopreserved cells were thawed in a water bath at 37° C. and the cell suspension transferred to a 15 mL tube containing 10 mL of RPMI1640 (Sigma) supplemented with 10% FBS (JRH Biosciences, catalogue 12003, lot 5J0174), 100 IU/mL penicillin (Sigma) and 100 μg/mL streptomycin (Sigma) (from now on referred to as RF10), or α-MEM (Sigma) supplemented with 10% FBS (JRH Biosciences), 100 IU/mL penicillin (Sigma) and 100 μg/mL streptomycin (Sigma) (from now on referred to as αMEM10). MV4; 11, MOLM13, HL60, KG1 and ME1 were cultured in RF10, and OCI-AML3 was cultured in α-MEM10. The cells were centrifuged at 400 g for 5 min, the supernatant was discarded and the cells were resuspended in 5 mL of RF10 or αMEM, respectively. Cells were cultured in humidified incubator with 5% CO$_2$ and split every 2-5 days to obtain a density of 2-5×10$^5$ cells/mL.

Cytotoxicity and Viability/Proliferation Assays)

The cell lines were plated in 96-well plates (black with clear flat bottom, Costar, 3603) at 2×10$^4$ cells/well in 50 uL of respective media, containing 0.1% DMSO and CellTox Green reagent (Promega, G8742) at a final dilution of 1/500. Cells were plated in triplicate wells for each dose being tested. EX 1 was reconstituted immediately prior to use at 10 mM in DMSO. The drug was prepared 2× concentrated in media containing 0.1% DMSO and 50 uL added to respective wells. Fluorescence (485-500 nm$_{Ex}$/520-530 nm$_{Em}$) was measured at 24 h and 48 h with a FLOUstar OPTIMA plate reader (BMG Labtech). After the cytotoxicity measurement at 48 h, 20 μL of CellTiter-Blue reagent (Promega, G8080) was added to each well and the plate incubated for 1 h at 37° C. before fluorescence (560$_{Ex}$/590$_{Em}$) was measured with a FLOUstar OPTIMA plate reader (BMG Labtech).

Total ROS Assay 1.25×10$^5$ cells were harvested into 5 mL tubes and washed with PBS. Cell pellets were resuspended in 180 μL of PBS and 20 μL of freshly prepared 5 mM CM-H2DCFDA (Molecular Probes, C6827) solution added to each tube. As positive control, one tube with cells harvested as above was prepared with 160 μL PBS, to resuspend the cell pellet, 20 μL of 10 μM tert-Butyl hydroperoxide (TBHP) and 20 μL of 5 mM CM-H2DCFDA. All tubes were incubated at 37° C. for 20 min and then cells washed 3 times with PBS. Cells were resuspended in 300 μL PBS and analysed on an LSRFortessa (BD Biosciences) flow cytometer. Results were analysed with FCS Express 4 Flow Research Edition software (De Novo Software).

Mitochondria O$_2^-$ Assay 1.25×10$^5$ cells were harvested into 5 mL tubes and washed with PBS. Cell pellets were resuspended in 180 μL of PBS and 20 μL of freshly prepared 5 mM MitoSox (Molecular Probes, M36008) solution added to each tube. All tubes were incubated at 37° C. for 20 min and then cells washed 3 times with PBS. Cells were resuspended in 300 μL PBS and analysed on an LSRFortessa (BD Biosciences)

flow cytometer. Results were analysed with FCS Express 4 Flow Research Edition software (De Novo Software).

Cell Cycle Assay $2 \times 10^5$ cells were harvested into 5 mL tubes and washed 3 times with PBS. Cell pellets were resuspended in 300 μL of cold PBS while vortexing. Next, cells were permeabilised with 700 μL of cold (−20° C.) 100% ethanol added dropwise while vortexing at slow speed. Cell suspensions were incubated on ice for 30 min, centrifuged at 300 g for 10 min and cell pellets resuspended in 100 μL PI solution (0.1% Triton X-100, 100 μg/mL DNAse-free RNAse A-Sigma, and 40 g/mL PI in PBS). Cell suspensions were incubated at 37° C. for 30 min in the dark. 200 μL of PBS was added to each tube before analysis on an LSRFortessa (BD Biosciences) flow cytometer. Results were analysed with FCS Express 4 Flow Research Edition software (De Novo Software).

Western Blot

Cells were harvested ($4 \times 10^6$ for cell lines and $7 \times 10^6$ for L-AMLs) and washed 3 times with cold PBS (centrifuged at 4° C.). Lysis buffer was prepared with NP40 Cell Lysis Buffer (ThermoFisher Scientific), cOmplete protease inhibitor (Roche, 046993116001), PhosStop (Roche, 04906837001) and Pefablock (Roche, 11585916001) at the recommended concentrations. After the washes, cells were resuspended in 50 μL of lysis buffer, vortexed and incubated on ice for 30 min. Samples were vortexed every 10 min. After 30 min incubation, samples were centrifuged at 14,000 g at 4° C. for 10 min and supernatants were transferred to tubes. Protein was quantified using the DC Protein Assay kit (BioRad) per manufacturer's protocol. 50 μg of cell lines lysate or 20 μg of L-AML6 lysate were loaded for SDS-PAGE. Protein was transferred from the gels into PVDF membranes using a semi dry transfer apparatus (BioRad). The membranes were blocked for 1 h at room temperature with 5% skim milk in 0.1% TBS-t and then incubated with gentle shaking with primary antibodies overnight at 4° C. Antibodies were diluted as follows: anti-Noxa (Calbiochem, catalogue OP1800-100UG, lot 2875160) 1:500 in 5% skim milk in 0.1% TBS-t, anti-P-JNK$^{Thr183/Tyr185}$ (Cell Signalling, catalogue 9255, lot 32) 1:1000 in 5% BSA in 0.1% TBS-t, and anti-tubulin (Santa Cruz Biotechnology, catalogue sc012462-R, lot C1516) 1:2000 in 5% skim milk in 0.1% TBS-t. The following morning, the membranes were washed 3 times with 0.1% TBS-t and incubated with respective secondary antibodies for 1 h at room temperature. Secondary antibodies anti-mouse-AP (Santa Cruz Biotechnology, catalogue sc-2308, lot G2409), for NOXA and P-JNK membranes, and anti-rabbit-AP (Santa Cruz Biotechnology, catalogue sc-2007, lot H2714), for tubulin probed membranes, were diluted 1:5000 in 5% skim milk in 0.1% TBS-t. For visualisation of results, membranes were scanned in a Typhoon FLA 9000 (GE Healthcare) scanner.

Tissue Culture—Primary Samples

Cryopreserved mononuclear cells (MNC from BM or leukapheresis samples) were thawed in a water bath at 37° C. and cell suspension transferred to a 50 mL tube. 20 mL of IMDM media (Sigma, 13390) supplemented with 20% FBS (JRH Biosciences), 50 U/mL DNase I (Sigma), 100 IU/mL penicillin (Sigma), 100 μg/mL streptomycin (Sigma) and 2 mM L-glutamine (Sigma) was added dropwise to the cells while the tube was being vortexed slowly (or mixed by hand). The cells were centrifuged at 400 g for 5 min, supernatant was discarded and the cells were washed once with 20 mL PBS. After the wash, the cells were resuspended in 25 mL IMDM (Sigma, 13390) supplemented with 20% FBS (JRH Biosciences), 100 IU/mL penicillin (Sigma), 100 μg/mL streptomycin (Sigma) and 2 mM L-glutamine (Sigma), and incubated overnight for recovery. The next morning, viability was determined by trypan blue exclusion and samples with viability lower than 85% underwent dead cell removal by density gradient centrifugation as follows: 15 mL of Lymphoprep (AXIS-Shield) was transferred to a 50 mL tube and the cell suspension (25 mL) carefully overlayed (so as not to disturb the interface mixing with the Lymphoprep). The tubes were centrifuged at 800 g for 20 min with acceleration set at 5 (half of the maximum) and no brake. MNC layer (formed in the interface between the media and the Lymphoprep) was transferred with a disposable Pasteur pipet into a 50 mL tube containing 20 mL PBS. The cells were centrifuged at 600 g for 5 min, supernatant discarded, and cell pellet resuspended in complete media containing IMDM (Sigma, 13390), 15% BIT (STEMCELL Technologies, 9500, lot 16L75786), 100 ng/mL hSCF (Peprotech, 300-07), 50 ng/mL hFlt3-Ligand (Peprotech, 300-19), 20 ng/mL hIL3 (Peprotech, 200-03), 20 ng/mL hG-CSF (Cell Signaling, 8930), $10^{-4}$M β-mercaptoethanol (BioRad), 0.5 μM SR1 (Selleckchem, S2858, lot 02) and 1 M UM729 (Selleckchem, S7510, lot S751001). Viability and cell density were determined by trypan blue exclusion and cells were plated for respective experiments as described in the Results section.

Caspase-Glo 3/7 Assay $10^4$ cells (10 μL) of each sample/treatment were aliquoted in triplicate wells of a 96-well plate (white wall OptiPlate 96, Perkin Elmer) containing 40 μL complete media. 50 μL of Caspase-Glo 3/7 reagent was added to each well, the plate was shaken for 30 sec at 300-500 rpm and incubated in the dark at room temperature for 30 min. Luminescence was measured with a FLOUstar OPTIMA plate reader (BMG Labtech).

Viability (Annexin V/7AAD) Assay $2 \times 10^5$ cells (200 μL) were harvested in 5 mL tubes and washed 3 times with PBS. Cell pellets were resuspended in 100 μL 1× binding buffer (BD Biosciences, 51-66121E) containing 2 μL of Annexin V-APC antibody (BD Biosciences, catalogue 550475, lot 6140584) and 2 μL of 7AAD solution (BD Biosciences, catalogue 51-68981E, lot 5006667-1), and incubated at room temperature in the dark for 30 min. 200 μL of PBS was added to the cell suspensions before analysis on an LSRFortessa (BD Biosciences) flow cytometer. Results were analysed with FCS Express 4 Flow Research Edition software (De Novo Software).

LSC Detection $8 \times 10^5$ cells (800 μL) were harvested in 5 mL tubes and fixed with 1.6% formaldehyde for 10 min at room temperature. The samples were then washed once with PBS and once with PBS/1% BSA. The cell pellets were resuspended in 100 μL PBS/1% BSA containing 5 μL of anti-CD34-APC (BD Biosciences, clone 8G12, catalogue 340441, lot 6183704), 5 μL of anti-CD38-PECy7 (BD Biosciences, 335790, lot 3353807) and 5 μL of anti-GPR56-PE (Biolegend, 358204, lot B208353) and incubated at room temperature for 1 h in the dark. Finally, cells were washed twice with PBS and resuspended in 200 μL of PBS for analysis on an LSR-Fortessa (BD Biosciences) flow cytometer. Results were analysed with FCS Express 4 Flow Research Edition software (De Novo Software).

Colony Assay 1.5 mL of Methocult H4034 (STEMCELL Technologies) was aliquoted in 5 mL tubes (one tube/treatment/sample) and supplemented with 20 ng/mL of hIL-6 (Peprotech, 200-06). EX 1 and OXi4503 dilutions were added to respective tubes to the final concentrations 100 nM and 500 nM. DMSO was used as vehicle control. Samples were added to each tube to the final cell density: $2 \times 10^4$ cells/well for L-AML6 and L-AML419, $3 \times 10^3$ cells/well for AML136 and AML480. The tubes were shaken to mix drugs and cells with the Methocult and incubated at 37° C. for 10 min to remove bubbles. Samples were then plated in 24-well plates, 4 wells/treatment/sample in the 8 wells at the centre of the plate. The wells at the edges were filled with sterile water to avoid drying. Plates were incubated at 37° C. for 13 days before colonies were counted.

MTS Proliferation Assay

The cell lines (MV4; 11 and HL-60) were plated in 96-well plates at $1 \times 10^4$ cells/well in 50 uL of complete growth media. Cells were plated in triplicate wells for each dose being tested. EX 1 (in DMSO), Oxi4503 (EndoTherm, Batch #EN09013, in water), CA4P (Selleckchem, Cat #S7204, in water) and Plinabulin (Selleckchem, Cat #S1176, in DMSO) was reconstituted immediately prior to use at 10 mM in appropriate diluent as indicated. The drug was prepared 2x concentrated in media and 50 uL added to respective wells (0.1% DMSO or water, final concentration). After 72 hours, 20 μL of CellTiter 96 AQueous One Solution reagent (Promega cat #G3581) was added to each well and the plate incubated for 2 h at 37° C. before absorbance was measured at 492 nm using a Thermo Multiskan Ascent96/384 Plate Reader.

1. Dose Response of AML Cell Lines to Example 1 (EX 1)

To test for cytotoxicity and anti-proliferative effect of EX 1 on AML cell lines, six different lines (Table 1) were thawed and cultured in respective media followed by treatment as described below.

TABLE 1

Detailed characteristics of AML cell lines used in this study

| Cell line | Details | FAB | Status |
|---|---|---|---|
| MV4; 11 | MLL translocation; MLL–AF4 AML (FLT3–ITD+) | M5 | diagnosis |
| MOLM13 | MLL translocation; MLL–AF9 AML --> after MDS (RAEB) (FLT3–ITD+) | M5a | relapse |
| ME1 | inv(16) | M4eo | 2nd relapse |
| KG1 | AML - erythroleukaemia that developed into AML at relapse | M0/M1 | relapse |
| HL60 | AML (APML) with PML–RARA gene fusion | M3 --> M2 | relapse |
| OCI-AML3 | AML – NPM1 and DNMT3A (R882C) mutation | M4 | diagnosis |

The first experiment was performed with HL60 and MOLM13 cell lines. Cells were expanded and when numbers were adequate (and viability higher than 90%) they were plated in 96-well plates at $2 \times 10^4$ cells/well in 50 uL of their respective media, containing 0.1% DMSO and CellTox Green reagent. Doses tested ranged from 1 μM followed by serial 1/10 dilutions until $10^{-5}$ nM EX 1, or vehicle only. Plates were cultured and fluorescence (indicating cytotoxicity) was measured at 24 h and 48 h. After the cytotoxicity was read at 48 h, CellTiter-Blue reagent was added to each well. The readout of this assay is based on the metabolic activity of cells and it is used as surrogate marker for proliferation and/or cell viability.

The next experiment was performed with the cell lines ME1, OCI-AML3, MV4; 11 and KG1 following the same protocol as above. From the results from the previous experiment it was observed that the non-linear curve fit was very steep between 1 nM and 0.1 nM (FIGS. 1A and B); thus, for this and the subsequent experiments the drug doses were adjusted to: 1 nM, 100 nM, 10 nM, 1 nM, 0.75 nM, 0.5 nM, 0.25 nM, 0.1 nM, 0.01 nM and 0.001 nM. The drug stock used was the one prepared one week previously for the HL60 and MOLM13 experiment, it was stored at −20° C. Cytotoxicity and proliferation (metabolic assay) were measured as above. Finally, an extra experiment was performed with MV4; 11 and MOLM13 with a freshly resuspended drug aliquot to confirm the results obtained. IC50 values are shown in FIGS. 1A and B. Where multiple experiments were performed, data was combined to determine the IC50.

As observed in FIGS. 1A and B, all cell lines showed sensitivity to EX 1 with very low IC50 doses, ranging from ~0.2 nM to 1.3 nM. Analysis of both cytotoxicity and proliferation experiments show that the cells segregate into two groups; the more sensitive cell lines (HL60, MOLM13 and MV4; 11) which reached the highest cytotoxicity and showed the largest inhibitory proliferation response; and the less sensitive cell lines (ME1, OCI-AML3 and KG1) which showed a lower cytotoxicity response and also maintained a reading above background for the CellTiter assay, consistent with some cell survival at the higher concentrations of the drug.

2. Investigating the Mechanism by which EX 1 Targets AML Cells

Once it was determined that this group of AML cell lines are highly sensitive to EX 1, the mechanism underlying this response was investigated. For that, cells were plated at $10^6$ cells/mL and treated with vehicle (DMSO) alone or a range of doses of EX 1 (0.1 nM, 1 nM, 10 nM and 100 nM) for 6 h, 8 h and 24 h. Cells were harvested for detection of ROS and superoxide anion ($O_2^-$) levels at 6 h and 24 h, for protein extraction at 8 h and 24 h, and for cell cycle analysis at 24 h.

2.1 Generation of Reactive Oxygen Species (ROS) by Cells Treated with EX 1

As it has been reported in the literature that KG1 cells treated with combretastatin-A4-P and OXi4500 (combretastatin-A1) show increase in total ROS levels (Petit et al. Blood 2008; Madlambayan et al. Blood 2010), ROS levels were measured in the 6 cell lines after 6 h and 24 h of treatment with a range of doses of EX 1. Total ROS levels were measured by flow cytometry using the fluorogenic dye CM-H2DCFDA at a final concentration of 5 μM. Mitochondria superoxide anion ($O_2^-$) levels were measured by flow cytometry using MitoSox, also at a final concentration of 5 μM.

Figure 2A:
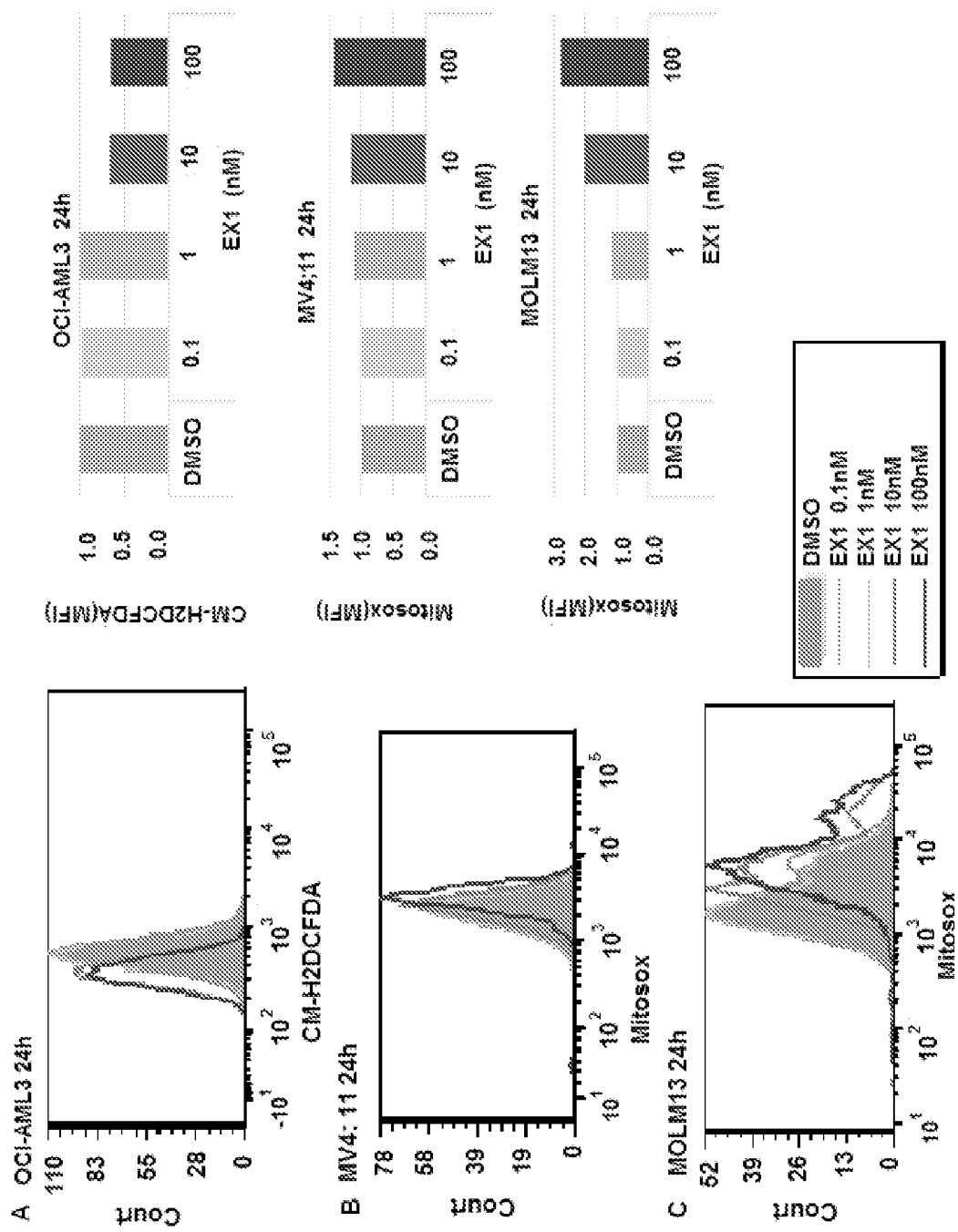
FIG. 2: A. Total ROS levels, measured by CM-H2DCFDA fluorescence, after EX 1 treatment of OCI-AML3 for 24 h. Values indicate mean fluorescence intensity (MFI) relative to untreated (DMSO) control.
Figure 2B:
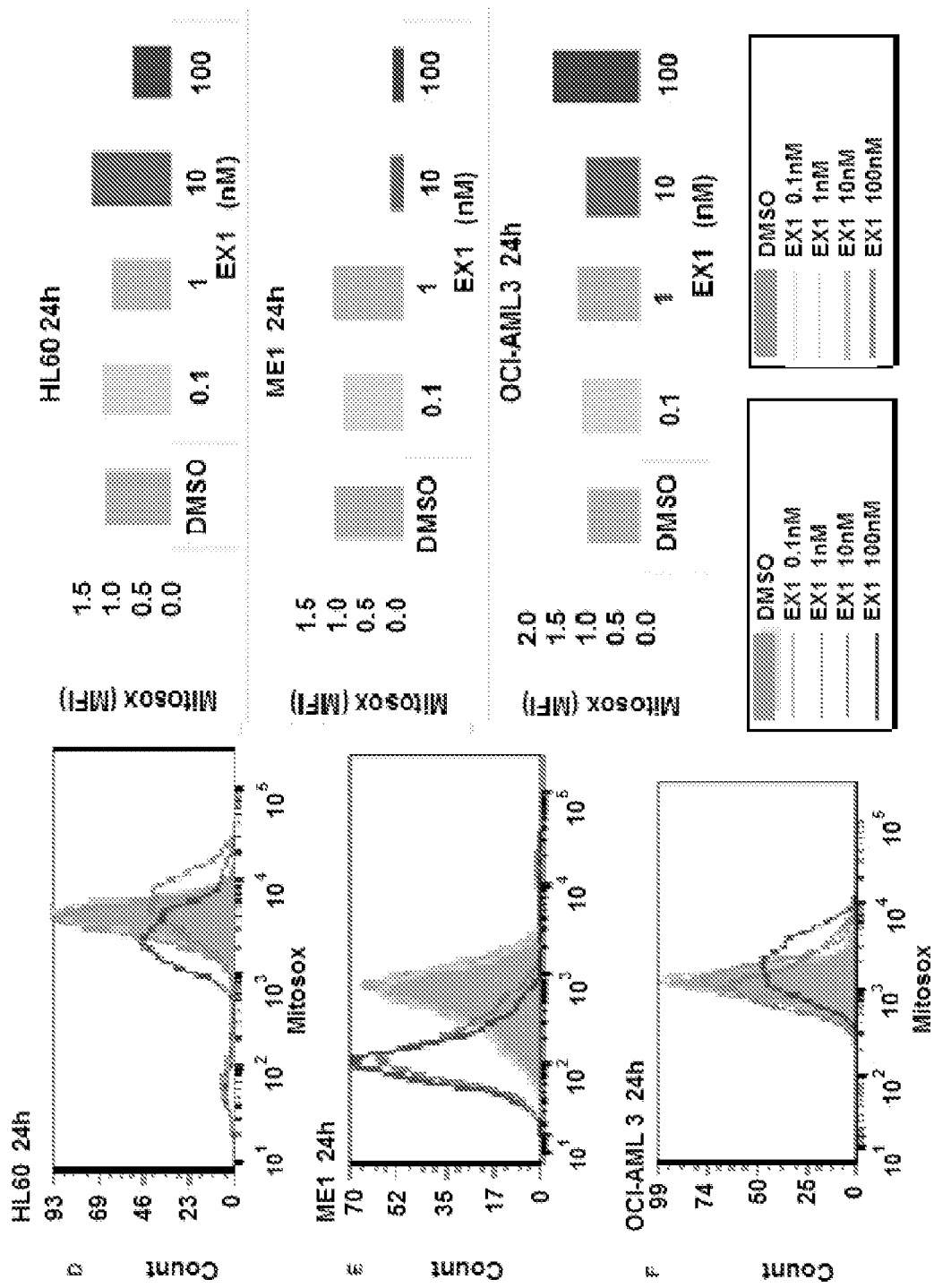

As shown in FIG. 2A, there was a dose response reduction in total ROS in OCI-AML3 cells after 24 h of treatment, however none of the other cell lines showed any changes in total ROS levels (data not shown). The levels of mitochondria $O_2^-$, on the other hand, changed in most of the cell lines, but with two different patterns. Both MV4; 11 and MOLM13 showed a dose response to the drug with increased mitochondria $O_2^-$ levels observed at 24 h only. The effect was much more pronounced in MOLM13 cells (FIG. 2B). HL60 and ME1, in contrast, showed a decrease in mitochondria $O_2^-$ levels at 6 h (data not shown) with an even greater effect observed at 24 h for the ME1 cells (FIG. 2B). While OCI-AML3 showed a slight decrease in mitochondria $O_2^-$ levels at 6 h, it appeared to have increased $O_2^-$ levels at 24 h (FIG. 2B). Finally, KG1 did not respond to the drug treatment with any detectable changes in mitochondria $O_2^-$.

2.2 Cell Cycle Analysis after Treatment of AML Cell Lines with EX 1

Petit and collaborators have also shown that in KG1 cells combretastatin-A4-P induces G2/M cell cycle arrest (Petit et al, Blood 2008). Therefore, cell cycle analysis was performed by PI staining in the cell lines after 24 h of treatment with a range of doses of EX 1, as described above.

As observed in FIG. 3, there were two patterns of cell cycle distribution after treatment with EX 1 for 24 h. The MV4; 11 and MOLM13 cells underwent apoptosis as evidenced by the increase in sub-G0 population; in addition, these cell lines showed a dose-dependent reduction in the percentage of cells in G2/M and G1. The second pattern was observed for the remaining cell lines, HL60, KG1, OCI-AML3 and ME1. Data for all of these cell lines was consistent with G2/M arrest in response to treatment with EX 1. KG1 and HL60 also showed marked increases in the sub-G0 cell population that were consistent with induction of apoptosis.

2.3 Activation of Pro-Apoptotic Signalling

EX 1 has been shown to induce apoptosis in chronic lymphocytic leukaemia (CLL) cells via phosphorylation of JNK (P-JNK) and induction of Noxa (Bates et al, Cancer Biol. Ther. 2016). Therefore, cells were treated with a range of doses of EX 1 for 8 h and 24 h, as described above, before protein extraction was performed. Western blot analysis showed that P-JNK$^{Thr183/Tyr185}$ was strongly induced in all cell lines at 8 h with 10 nM and 100 nM of EX 1 (FIG. 4). Induction of Noxa, on the other hand, could only be detected in OCI-AML3 and ME1, both with 10 nM and 100 nM of drug and after 8 h of treatment. Noxa was readily detected in control lysate prepared from HEK293 cells.

Taken together, these results suggest that, even though EX 1 induces JNK activation consistently across AML cell lines, it is likely that the mechanism of apoptosis or cell cycle arrest is cell type-dependent. MV4; 11 and MOLM13 show a similar response to EX 1 based on cytotoxicity, mitochondria $O_2^-$ and cell cycle, while the other group (KG1, ME1 and OCI-AML3) show a similar lower level of cytotoxicity response and cell cycle distribution.

3. Targeting of Primary AML Cells by EX 1

Having established that AML cell lines are sensitive to EX 1, and partially investigated the mechanism by which the drug induces cell death in those lines, the next step was to determine the sensitivity of primary AML samples to the compound. For these experiments cryopreserved de-identified AML samples (mononuclear cells, MNC) were retrieved from the SACRB Biobank under Ethics Approval (R20170220) from the Royal Adelaide Human Research Ethics Committee (RAH HREC).

AML Bone Marrow Specimens

An experiment was performed using three healthy control (HC) BMMNC samples (HC61, HC68 and HC71) and additional AML samples (MNC isolated from bone marrow diagnostic specimens, Table 2). As detailed in Material and Methods, the cells were thawed, recovered overnight in described media, and viability and cell number checked (by trypan blue exclusion) the next day. After overnight recovery and viability check, two samples (AML235 and AML342) were purified by density gradient centrifugation with Lymphoprep to remove dead cells. Viable cell recovery from AML342 after purification was insufficient to proceed with the experiment, so this sample was not used. HCs were plated at $10^6$ cells/mL (500 μL/well in duplicate wells) in 24-well plates and the AMLs at $10^6$ cells/mL in 2 mL/well/dose in 6-well plates. As there are less cells available from the BM AML samples compared to the L-AML (leukapheresis), these samples were not plated for preparation of protein lysate, but only for antibody staining and flow cytometric analysis (Annexin V/7AAD, and co-staining for CD34, CD38 and GPR56 to detect the leukaemic stem cell, LSC, population). AML samples were also plated in colony assays to determine the effect of EX 1 on AML blast-forming cells.

TABLE 2

Characteristics of AML primary samples used in this study

| Sample | Results obtained | Blast % | Karyotype | Cytogenetics | Somatic mutations | FAB | Notes |
|---|---|---|---|---|---|---|---|
| L-AML6 | Y | 70% (PB) | Normal | | FLT3–ITD, WT1, IDH1 | M4 | |
| L-AML7 | N | 98% (PB) | Normal | | FLT3–ITD, NPM1 | M1 | |
| L-AML418 | N | 97% (PB) | Abnormal | ?MLL, –Y | | M5 | t-AML |
| L-AML419 | Y | 99% (BM) | Normal | | | M1 | |
| AML136 | Y | 95% (BM) | Abnormal | MLL | | M5 | |
| AML235 | Y | 73% (BM) | Abnormal | t(6; 9) | | M2 | |
| AML342 | N | 86% (BM) | Normal | | NPM1, IDH2 | M2 | |
| AML480 | Y | 96% (BM) | Normal | | NPM1 | M1 | |

PB: peripheral blood;
BM: bone marrow;
?MLL: possible MLL alteration;
t-AML: therapy related AML.

Viability. After 24 h of treatment, 10 μL of cells were used in the Caspase-Glo 3/7 assay, as before, and once more little to no caspase activation was observed (FIG. 5A). Only AML480 showed some increase in caspase activity for the cells treated with EX 1, but the activity for the cells in DMSO was already high, which means the sample viability was low. Based on this result, the samples were cultured for another day when the Caspase-Glo 3/7 assay was performed once more. At the 48 h time point there was an increase in caspase activity for all the AML samples treated with EX 1 compared to DMSO (FIG. 5B). 200 μL of the cells from all samples was then harvested for Annexin V/7AAD staining, and 800 µL of the AML cultures was used for CD34, CD38 and GPR56 staining. The remaining cells were cultured for one more day and harvested at 72 h for the same assays. As observed in the previous experiment, the HC samples showed some reduced viability at 48 h in the presence of EX 1 (FIG. 5C), but the viability remained stable up to 72 h (FIG. 5D). The response of the AML samples to the drug, however, progressed with time with viability decreasing substantially from 48 h to 72 h (FIGS. 5C and D). The samples used in this experiment (HC and AML) also did not show a response to treatment with OXi4503.

LSC analysis. AML BMMNC samples were first gated for viable cells and then the fraction of GPR56+ cells was determined. According to the report by Pabst and collaborators (Pabst et al, Blood 2016), in CD34$^{high}$ AML samples the GPR56+ population containing LSCs is present within the CD34+ cells, while in CD34$^{low}$ AML samples the GPR56+ population containing LSCs is present in both CD34+ and CD34− cell populations. Therefore, the LSC containing subpopulation was estimated from the CD34+/GPR56+ gate for AML235, and from the GPR56+/CD34+ and GPR56+/CD34− gates in AML136 and AML480 (FIG. 6A). A decrease in these subpopulations in response to EX 1 would be consistent with the drug targeting the important LSC-containing compartment. As shown in FIG. 6B, the flow cytometry analysis indicated that this cell population is affected at different rates by EX 1 in a sample-dependent manner. On the other hand, OXi4503 treatment, when compared to vehicle control (DMSO), had little effect on AML136 and no effect on AML235 and AML480 (FIG. 6B). As shown in FIG. 6C, EX 1 is potent at decreasing the LSC population at concentration as low as 20 nM.

Blast cell colony assay. For colony assays AML MNC were plated in methylcellulose with added cytokines (see Methods) and colonies scored after 13 days. From the 4 samples plated, AML136 and AML480 did not grow any colonies in vehicle, EX 1 or OXi4503. For L-AML6 a small number of colonies and a high background of single cells (i.e. cells that stay alive in the semi-solid media but do not form colonies) were observed in the vehicle treated wells. In contrast, no colonies or background cells were observed in the wells with either dose of EX 1 (FIG. 7A). Treatment of this sample with OXi4503 at 100 nM reduced the background cells and also the number of colonies, while 500 nM completely blocked colony formation and the background of viable cells (FIG. 7A). L-AML419 also formed a small number of colonies in the DMSO-treated wells, with fewer background cells. Treatment with both drugs (all doses) completely blocked colony and background formation for this sample (FIG. 7B).

Western blot analysis. Protein lysate was prepared for two of the AML samples (L-AML6 and L-AML419) after 48 h of treatment. For sample L-AML419 insufficient protein was recovered for western blot analysis. For L-AML6 cells P-JNK$^{Thr183/Tyr185}$ and Noxa expression were determined using the specific antibodies that have been validated in the cell line experiments (FIG. 4). A small increase in P-JNK$^{Thr183/Tyr185}$ was observed for cells treated with EX 1 at 500 nM with no apparent change for OXi4503 treatment (FIG. 8). Noxa expression was detectable but very low in this sample and no change was observed with either drug treatment. An important point to consider here is that the protein yield from this sample was very low and only 20 µg of protein was loaded for SDS-PAGE, while 50 µg of protein was used for cell line samples.

Comparison of EX 1 with Other Tubulin Polymerisation Inhibitors

To compare the efficacy of EX 1 with other tubulin polymerisation inhibitors, MTS proliferation assays were performed on MV4;11 and HL-60 AML cell lines (Table 1). Cells were expanded and when numbers were adequate (and viability higher than 90%) they were plated in 96-well plates at 1×10$^4$ cells/well in 100 uL of complete growth media, containing a final concentration of 0.1% DMSO or water. EX 1, Oxi4503 (EndoTherm, Batch #EN09013, in water), CA4P (Selleckchem, Cat #S7204, in water) and Plinabulin (Selleckchem, Cat #S1176, in DMSO) were tested in serial 1/10 dilutions from 0.00001 nM-1000 nM. Cells were cultured with the compounds for 72 hours before viability was measured by the addition of CellTiter 96 AQueous One Solution reagent (Promega cat #G3581) and absorbance measured at 492 nm. IC50 was calculated using the absolute IC50 method in GraphPad Prism 6. As demonstrated in FIG. 9, EX 1 has the lowest IC50 in both AML cell lines, indicating that it is more potent than the other tubulin polymerisation inhibitors tested.

The invention claimed is:

1. A method for treating acute myeloid leukemia (AML) in a patient in need thereof comprising administering to the patient an effective amount of a compound of formula (I) or a salt, solvate or prodrug thereof

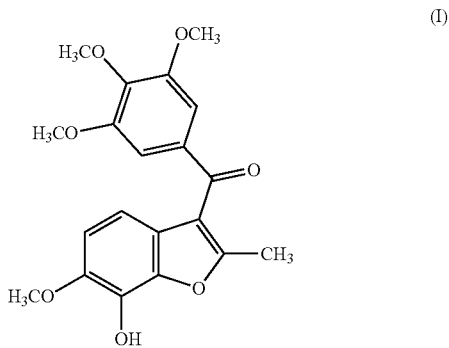 [SMILES: COc1cc(C(=O)c2c(C)oc3c(O)c(OC)ccc23)cc(OC)c1OC]

wherein the effective amount administered to the patient is from about 0.05 to 18 mg/kg body weight per day.

2. The method of claim 1 wherein the patient is a human subject.

3. The method of claim 1 wherein the effective amount administered is from about 0.4 mg to 16 mg/kg body weight per day.

4. The method of claim 1 wherein the compound is administered by parenteral administration.

5. The method of claim 1 wherein the compound is co-administered simultaneously or sequentially with another anti-cancer agent.

6. The method of claim 1 wherein the patient is selected for treatment based on clinical parameters including age, level of progression of the disease, and/or other complicating ailments.

7. A pharmaceutical kit for treating AML in a patient in need thereof comprising the compound of formula (I):
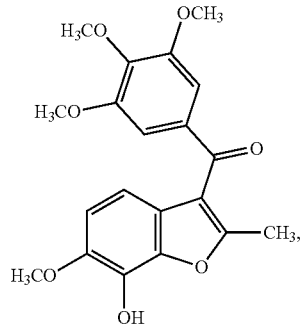
together with instructions for administering the compound to the patient.
8. The method according to claim 1 wherein the compound of formula (I) is:
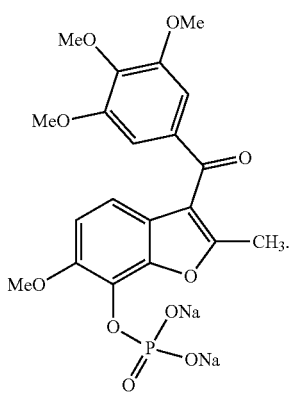
* * * * *